US008309065B2

(12) United States Patent
Ansmann et al.

(10) Patent No.: US 8,309,065 B2
(45) Date of Patent: *Nov. 13, 2012

(54) HYDROCARBON MIXTURE AND USE THEREOF

(75) Inventors: Achim Ansmann, Erkrath (DE); Markus Dierker, Duesseldorf (DE); Rolf Kawa, Monheim (DE); Yeah-Young Baek, Duisburg (DE); Bettina Jackwerth, Langenfeld (DE)

(73) Assignee: Cognis IP Management GmbH, Duesseldorf (DE)

( * ) Notice: Subject to any disclaimer, the term of this patent is extended or adjusted under 35 U.S.C. 154(b) by 176 days.

This patent is subject to a terminal disclaimer.

(21) Appl. No.: 12/665,425

(22) PCT Filed: Jun. 12, 2008

(86) PCT No.: PCT/EP2008/004699
§ 371 (c)(1),
(2), (4) Date: Dec. 18, 2009

(87) PCT Pub. No.: WO2008/155057
PCT Pub. Date: Dec. 24, 2008

(65) Prior Publication Data
US 2010/0183536 A1    Jul. 22, 2010

(30) Foreign Application Priority Data

Jun. 19, 2007 (EP) .................................. 07011967
Jun. 20, 2007 (EP) .................................. 07075513
Mar. 4, 2008 (DE) ........................ 10 2008 012 458

(51) Int. Cl.
*A61K 8/31*     (2006.01)
*A61K 47/06*    (2006.01)

(52) U.S. Cl. ........................................ 424/65; 514/772
(58) Field of Classification Search .................... 424/65; 514/772
See application file for complete search history.

(56) References Cited

U.S. PATENT DOCUMENTS

| 2008/0161418 | A1  | 7/2008  | Dierker |
| 2010/0260701 | A1* | 10/2010 | Dop ........................... 424/78.03 |
| 2011/0059032 | A1* | 3/2011  | Dierker et al. ................... 424/59 |
| 2011/0139171 | A1* | 6/2011  | Bonnamy et al. ............. 132/206 |
| 2011/0150801 | A1* | 6/2011  | Lebre-Lemonnier ........... 424/63 |
| 2011/0305656 | A1* | 12/2011 | Grandjon ........................ 424/65 |

FOREIGN PATENT DOCUMENTS

| CA | 2607229 A1 | 11/2006 |
| EP | 0388110 A1 | 9/1990 |
| EP | 0693471 B1 | 1/1996 |
| EP | 0694521 B1 | 1/1996 |
| EP | 0766661 B1 | 4/1997 |
| JP | 03009999 | 1/1991 |
| WO | 98/58623 A1 | 12/1998 |
| WO | 2004/011581 A1 | 2/2004 |
| WO | 2005/063189 A1 | 7/2005 |
| WO | 2006/094642 A1 | 9/2006 |
| WO | 2006/120003 A1 | 11/2006 |
| WO | 2007/048757 A1 | 5/2007 |
| WO | 2007/068371 A1 | 6/2007 |

OTHER PUBLICATIONS

Handbook of Cosmetic Science and Technology Barel et al.; Marcel Dekker Inc. 2001.
"Lexikon der Hilfsstoffe fur Pharmazie, Kosmetik und angrenzende Gebiete" H. P. Fielder Aulendorf, 4. Aufl. 1996.
"Diuretics to Emulsions" Encyclopedia of Chemical Technology Kirk-Othmer; Third Edition, vol. 8, 1979; p. 913.
Commission Directive 2005/9/EC of Jan. 28, 2005 amending Council Directive 76/768/EEC, concerning cosmetic products, for the purposes of adapting Annex VII thereto to technical progress; pp. 27/46-27/47.
"Formulierung kosmetischer Sonnenschutzmittel" P. Finkel SOFW-Journal 122, Jahrgang Aug. 1996, pp. 543-548, Summary only.
"Identification of the Sex Pheromone of an Ant, *Formica lugubris* (Hymenoptera, Formicidae)" F. Walter et al. Naturwissenschaften, Springer, Berlin, DE Bd. 80, Jan. 1, 1993, pp. 30-34 XP007909550.
International Search Report from PCT/EP2008/004699 dated Sep. 24, 2009.

* cited by examiner

*Primary Examiner* — Aradhana Sasan
(74) *Attorney, Agent, or Firm* — Diehl Servilla LLC

(57) ABSTRACT

The invention relates to hydrocarbon mixtures containing linear C11 and linear C13 hydrocarbons, wherein the sum of the linear C11 and linear C13 hydrocarbons is greater than or equal to 60 wt. % with relation to the sum of the hydrocarbons, and to the use of said mixtures in cosmetic and/or pharmaceutical preparations.

20 Claims, No Drawings

HYDROCARBON MIXTURE AND USE THEREOF

CROSS REFERENCE TO RELATED APPLICATIONS

This application is the National Phase entry of PCT/EP2008/004699, filed Jun. 12, 2008, which claims priority to European patent application number EP07011967.2 filed Jun. 19, 2007, European patent application number 07075513.7, filed Jun. 20, 2007, and German patent application number 10 2008 012 458.3, filed Mar. 4, 2008, all of which are incorporated herein by reference in their entireties.

FIELD OF THE INVENTION

The present invention relates to hydrocarbon mixtures, to the use thereof in cosmetic and/or pharmaceutical formulations, and to cosmetic and/or pharmaceutical formulations comprising hydrocarbon mixtures.

BACKGROUND OF THE INVENTION

Sensorily light oil bodies, known as "light emollients", are used by the cosmetics industry in a multitude of formulations. Especially for decorative cosmetics or in care formulations, what are known as "light" components are used. These components may, for example, be volatile, cyclic silicones (e.g. cyclopentasiloxane or cyclomethicone) or hydrocarbons from petrochemical processes. Owing to their preparation, the latter substances are predominantly mixtures of linear, cyclic and branched hydrocarbons whose flashpoint may quite possibly be below 50° C. (as, for example, in the case of isododecane). Examples and application-related descriptions of such formulations can be found in standard works, for example: "Handbook of Cosmetic Science and Technology", A. Barel, M. Paye, H. Maibach, Marcel Dekker Inc. 2001. For toxicological, ecological and safety reasons, however, there will in the future be a demand for alternative raw materials for such formulation tasks.

Substances used in cosmetic and pharmaceutical formulations under the name "mineral oil" include the liquid distillation products which are obtained from mineral raw materials (mineral oil, brown and hard coals) and consist essentially of mixtures of saturated hydrocarbons with linear, cyclic and/or branched structure. These hydrocarbon mixtures must, however, be purified and chemically modified in a complicated manner before they meet the demands on cosmetic raw materials.

It was an object of the invention to find alternative raw materials which are ecologically and toxicologically uncontroversial. More particularly, it was of interest to provide raw materials which can be used directly in cosmetic or pharmaceutical formulations without complicated purification steps. These raw materials should preferably be obtainable on the basis of renewable raw materials. These raw materials should be usable directly in typical cosmetic and/or pharmaceutical formulations without application-related restrictions. Furthermore, the raw materials should have improved sensory properties over the hydrocarbon mixtures of the prior art, and it would also be desirable that these raw materials have a better skin compatibility. It was of particular interest to provide raw materials whose possible uses with regard to formulation or sensory properties are comparable to those of silicone oils, especially to those of low-viscosity silicone oils, for example dimethicones. It was desirable, more particularly, to provide raw materials which are suitable as substitutes for silicone oils. It was additionally of interest to provide raw materials which have an improved $CO_2$ balance compared to the prior art raw materials.

It was a further object to provide raw materials which enable a stable formulation with AP/Deo (=antiperspirant/deodorant) active ingredients. Cosmetic formulations for the antiperspirants/deodorants category, especially in so-called "stick formulations", still have the problem of insufficient stability of the cosmetic base. In this context, one property in need of improvement is the hardness of the "stick formulation" produced. A disadvantage of existing "stick formulations" is that changes in odor arise during storage. It is therefore a further object of the invention to provide raw materials which enable antiperspirant or deodorant formulations, especially those in "stick formulations", to be provided in stable form. These formulations should not exhibit any undesired evolution of odor, especially in the course of prolonged storage. It was a further object to provide raw materials which impart a sensorily "light" impression, if at all possible with simultaneously improved skin compatibility, especially in combination with UV light protection filters and in combination with self-tanning agents. Of particular interest is the provision of novel raw materials which enable a sensorily advantageous impression in decorative cosmetics formulations. Owing to the site of application (principally face and hands), increased demands are made on the sensory properties, especially the volatility, on formulations in decorative cosmetics, for example lipsticks, eyeshadow, mascara, nail varnish, etc., in order that these products do not give the impression of "heaviness". In addition, good dispersibility of pigments is desirable in these products.

DETAILED DESCRIPTION OF PREFERRED EMBODIMENTS

The invention provides hydrocarbon mixtures comprising linear C11 and linear C13 hydrocarbons, the sum of the linear C11 and linear C13 hydrocarbons being greater than or equal to 60% by weight, based on the sum of the hydrocarbons.

The parameter "sum of the hydrocarbons" includes all hydrocarbons present in the mixture, irrespective of their carbon number.

Hydrocarbons refer to organic compounds which consist only of carbon and hydrogen. They include both cyclic and acyclic (=aliphatic) compounds. They include both saturated and mono- or polyunsaturated compounds. The hydrocarbons may be linear or branched. According to the number of carbon atoms in the hydrocarbon, the hydrocarbons can be divided into odd-numbered hydrocarbons (for example nonane, undecane, tridecane) or even-numbered hydrocarbons (for example octane, dodecane, tetradecane). According to the type of branching, the hydrocarbons can be divided into linear (=unbranched) or branched hydrocarbons. Saturated aliphatic hydrocarbons are also referred to as paraffins.

A "hydrocarbon mixture" in the context of the invention is understood to mean mixtures of hydrocarbons which contain up to 10% by weight of substances which are not hydrocarbons. The percentages by weight of the linear C11 and linear C13 hydrocarbons are based in each case on the sum of the hydrocarbons present in the mixture. The nonhydrocarbons which are present up to 10% by weight are not considered for this calculation.

The substances which are not hydrocarbons and which may be present up to 10% by weight, especially up to 8% by weight, preferably up to 5% by weight, in the inventive hydrocarbon mixture are, for example, fatty alcohols, which remain in the hydrocarbon mixture as unconverted reactants.

The term "CX hydrocarbon" encompasses hydrocarbons having a carbon number of X (where X is an integer); for example, the term "C11 hydrocarbon" encompasses all hydrocarbons with a carbon number of 11. The term "carbon number" encompasses all carbon atoms present in the hydrocarbon. It is thus, for example, 11 for undecane or 13 for tridecane.

A preferred embodiment of the invention relates to hydrocarbon mixtures, wherein the mixture comprises
  (a) 50 to 90% by weight of linear C-11 hydrocarbons, preferably n-undecane
  (b) 10 to 50% by weight of linear C13 hydrocarbons, preferably n-tridecane
based on the sum of the hydrocarbons.

Particular preference is given to hydrocarbon mixtures which comprise
  (a) 55 to 80% by weight, especially 60 to 75% by weight, especially 65 to 70% by weight, of linear C-11 hydrocarbons, preferably n-undecane
  (b) 20 to 45% by weight, especially 24 to 40% by weight, especially 24 to 30% by weight, of linear C-13 hydrocarbons, preferably n-tridecane
based on the sum of the hydrocarbons.

A preferred embodiment of the invention relates to hydrocarbon mixtures, characterized in that the sum of the linear C11 and linear C13 hydrocarbons is greater than or equal to 70% by weight, especially greater than or equal to 80% by weight, preferably greater than or equal to 90% by weight, more preferably greater than or equal to 95% by weight, especially greater than or equal to 99% by weight, based on the sum of the hydrocarbons.

In a preferred embodiment of the invention, the weight ratio of linear C11 hydrocarbons to linear C13 hydrocarbons is 1.5 to 3.5.

In a preferred embodiment of the invention, the inventive hydrocarbon mixture comprises less than or equal to 40% by weight, especially less than or equal to 20% by weight, especially less than or equal to 10% by weight, preferably less than or equal to 8% by weight, preferably less than or equal to 5% by weight, preferably less than or equal to 3% by weight, preferably less than or equal to 2% by weight, especially less than or equal to 1% by weight, of branched hydrocarbons, based on the sum of the hydrocarbons.

A preferred embodiment of the invention relates to hydrocarbon mixtures comprising linear C11 and linear C13 hydrocarbons, wherein the sum of the linear C11 and linear C13 hydrocarbons is greater than or equal to 60% by weight, based on the sum of the hydrocarbons, and wherein the sum of the branched hydrocarbons is less than or equal to 10% by weight, based on the sum of the hydrocarbons.

Particular preference is given to hydrocarbon mixtures comprising linear C11 and linear C13 hydrocarbons, wherein the sum of the linear C11 and linear C13 hydrocarbons is greater than or equal to 60% by weight, based on the sum of the hydrocarbons, and wherein the sum of the branched hydrocarbons is less than or equal to 8% by weight, especially less than or equal to 5% by weight, especially less than or equal to 3% by weight, preferably less than or equal to 2% by weight, based on the sum of the hydrocarbons. In a preferred embodiment of the invention, the sum of the branched hydrocarbons is less than or equal to 1% by weight, based on the sum of the hydrocarbons.

In a preferred embodiment of the invention, the inventive hydrocarbon mixture comprises less than or equal to 20% by weight, especially less than or equal to 10% by weight, preferably less than or equal to 8% by weight, preferably less than or equal to 5% by weight, preferably less than or equal to 3% by weight, preferably less than or equal to 2% by weight, especially less than or equal to 1% by weight, of aromatic hydrocarbons—based on the sum of the hydrocarbons. In a preferred embodiment of the invention, the inventive hydrocarbon mixture comprises less than 0.1%, especially less than 0.01% and especially less than 0.001% by weight of aromatic hydrocarbons, based on the sum of the hydrocarbons.

In a preferred embodiment, the inventive hydrocarbon mixture comprises less than or equal to 50% by weight, preferably less than or equal to 40% by weight, especially less than or equal to 20% by weight, especially less than or equal to 10% by weight, preferably less than or equal to 8% by weight, preferably less than or equal to 5% by weight, preferably less than or equal to 3% by weight, preferably less than or equal to 2% by weight, especially less than or equal to 1% by weight, of unsaturated hydrocarbons, based on the sum of the hydrocarbons. In a preferred embodiment of the invention, the inventive hydrocarbon mixture comprises less than or equal to 0.1%, especially less than or equal to 0.01% and especially less than or equal to 0.001% by weight of unsaturated hydrocarbons, based on the sum of the hydrocarbons.

In a preferred embodiment, the inventive hydrocarbon mixture comprises less than or equal to 20% by weight, especially less than or equal to 15% by weight, especially less than or equal to 10% by weight, preferably less than or equal to 9% by weight, preferably less than or equal to 8% by weight, preferably less than or equal to 5% by weight, of even-numbered hydrocarbons, based on the sum of the hydrocarbons.

Particular preference is given to hydrocarbon mixtures in which the linear C11 and/or linear C13 hydrocarbons are saturated hydrocarbons; both the linear C11 and the linear C13 hydrocarbons are preferably a linear hydrocarbon (n-undecane and n-tridecane).

In a preferred embodiment, the inventive hydrocarbon mixtures comprise less than or equal to 10% by weight, especially less than or equal to 5% by weight, preferably less than or equal to 3% by weight, of C-12 hydrocarbons, based on the sum of the hydrocarbons.

A preferred embodiment of the invention relates to hydrocarbon mixtures comprising linear C11 and linear C13 hydrocarbons, wherein the sum of the linear C11 and linear C13 hydrocarbons is greater than or equal to 60% by weight, based on the sum of the hydrocarbons, and wherein the sum of the hydrocarbons having a carbon chain length greater than or equal to 14 is less than or equal to 15% by weight, based on the sum of the hydrocarbons. Particular preference is given to hydrocarbon mixtures in which the sum of the hydrocarbons having a carbon chain length greater than or equal to 14 is less than or equal to 10% by weight, especially less than or equal to 8% by weight, preferably less than or equal to 4% by weight, especially less than or equal to 2% by weight, based in each case on the sum of the hydrocarbons.

A preferred embodiment of the invention relates to hydrocarbon mixtures comprising linear C11 and linear C13 hydrocarbons, wherein the sum of the linear C11 and linear C13 hydrocarbons is greater than or equal to 60% by weight, based on the sum of the hydrocarbons, and the sum of the hydrocarbons having a carbon chain length of less than or equal to 10 is less than or equal to 3% by weight, especially less than or equal to 2% by weight, preferably less than or equal to 1.5% by weight, especially less than or equal to 1% by weight, based on the sum of the hydrocarbons.

In one embodiment of the invention, the inventive hydrocarbon mixtures comprise C12 and C14 hydrocarbons, preferably in the same weight ratio relative to one another as the linear C11 hydrocarbons to the linear C13 hydrocarbons. In a preferred embodiment of the invention, both the weight ratio of linear C11 hydrocarbons to linear C13 hydrocarbons and the weight ratio of C12 to C14 hydrocarbons are 1.5 to 3.5.

In one embodiment of the invention, the hydrocarbons in the inventive hydrocarbon mixture consist of hydrocarbons having 7 to 23 carbon atoms, preferably 9 to 21 carbon atoms, especially preferably 11 to 17 carbon atoms.

The inventive hydrocarbon mixtures are suitable especially for use in cosmetic and/or pharmaceutical formulations, especially as oil bodies and/or dispersants.

The invention further provides a process for producing a cosmetic and/or pharmaceutical formulation, wherein a hydrocarbon mixture as claimed in any of claims 1 to 10 is added to a cosmetically and/or pharmaceutically suitable carrier.

The inventive hydrocarbon mixtures are suitable especially for use in cosmetic formulations for care of skin and/or hair.

The inventive hydrocarbon mixtures are suitable especially for use in cosmetic formulations for sun protection.

The inventive hydrocarbon mixtures are suitable especially for use in decorative cosmetics formulations, for example lipsticks, lip gloss, eyeshadow, mascara, eye pencils (kohl), nail varnish, and in makeup formulations of any kind (powders, creams, foundations, coversticks, etc.).

The inventive hydrocarbon mixtures are suitable especially for use in formulations for cleaning skin and/or hair, for example shampoos, shower gels, bath additives, conditioners, etc.

The inventive hydrocarbon mixtures are also suitable for producing finely divided emulsions, for example nanoemulsions, microemulsions or PIT emulsions. In such finely divided emulsions, the oil droplets are generally present with a diameter in the range from 10 to 1000 nm, preferably 100 to 500 nm. These are produced by processes known to those skilled in the art, described for PIT emulsions, for example, in Parfümerie and Kosmetik [Perfumery and Cosmetics], volume 77, no. 4/96, p. 250-254, by Wadle et al.

Production of the Hydrocarbon Mixtures

The inventive hydrocarbon mixtures can be obtained, for example, by blending linear C11 and linear C13 hydrocarbons. In addition, they can be obtained, for example, by reductive demethylation by methods known to those skilled in the art. A particularly suitable process for producing the inventive hydrocarbon mixtures is the process for reductive dehydroxymethylation proceeding from fatty alcohols of vegetable origin, described in international application PCT/EP2006/011647 (Cognis). In this process, for example, C12 and C14 fatty alcohols can be subjected individually to the process described, and the C11 and C13 hydrocarbons thus obtained can be mixed to give the inventive hydrocarbon mixtures. It is preferred, however, to subject a mixture of C12 and C14 fatty alcohols which comprises at least 60% by weight of C12 and C14 fatty alcohols to the reductive dehydroxymethylation, such that the reaction product obtained directly is the inventive hydrocarbon mixture. This can then be used directly, without further purification, in cosmetic and/or pharmaceutical formulations.

Cosmetic and/or Pharmaceutical Formulations

The invention further provides cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons.

A preferred embodiment of the invention relates to cosmetic and/or pharmaceutical formulations comprising 1 to 80% by weight, preferably 5 to 50% by weight, of hydrocarbons which comprise linear C11 and linear C13 hydrocarbons, wherein the sum of the linear C11 and linear C13 hydrocarbons is greater than or equal to 60% by weight, based on the sum of the hydrocarbons.

The parameter "sum of the hydrocarbons" encompasses all hydrocarbons present in the cosmetic and/or pharmaceutical formulation, irrespective of their carbon number.

The term "% by weight of hydrocarbons" always relates—unless stated otherwise—to the total weight of the cosmetic and/or pharmaceutical formulation.

These cosmetic and/or pharmaceutical formulations may accordingly comprise further hydrocarbons, for example paraffins or waxes, provided that the sum of the linear C11 and linear C13 hydrocarbons is greater than or equal to 60% by weight, based on the sum of the hydrocarbons.

In a preferred embodiment of the invention, the inventive cosmetic and/or pharmaceutical formulations comprise hydrocarbon mixtures which comprise less than or equal to 40% by weight, especially less than or equal to 20% by weight, especially less than or equal to 10% by weight, preferably less than or equal to 8% by weight, preferably less than or equal to 5% by weight, preferably less than or equal to 3% by weight, preferably less than or equal to 2% by weight, especially less than or equal to 1% by weight, of branched hydrocarbons, based on the sum of the hydrocarbons.

In a preferred embodiment of the invention, the inventive cosmetic and/or pharmaceutical formulations comprise hydrocarbon mixtures which comprise less than or equal to 20% by weight, especially less than or equal to 10% by weight, preferably less than or equal to 8% by weight, preferably less than or equal to 5% by weight, preferably less than or equal to 3% by weight, preferably less than or equal to 2% by weight, especially less than or equal to 1% by weight, of aromatic hydrocarbons—based on the sum of the hydrocarbons. In a preferred embodiment of the invention, the inventive formulation comprises less than 0.1%, especially less than 0.01% and especially less than 0.001% by weight of aromatic hydrocarbons, based on the sum of the hydrocarbons.

In a preferred embodiment, the inventive cosmetic and/or pharmaceutical formulations comprise hydrocarbon mixtures which comprise less than or equal to 50% by weight, preferably less than or equal to 40% by weight, especially less than or equal to 20% by weight, especially less than or equal to 10% by weight, preferably less than or equal to 8% by weight, preferably less than or equal to 5% by weight, preferably less than or equal to 3% by weight, preferably less than or equal to 2% by weight, especially less than or equal to 1% by weight, of unsaturated hydrocarbons, based on the sum of the hydrocarbons. In a preferred embodiment of the invention, the formulations comprise less than or equal to 0.1%, especially less than or equal to 0.01% and especially less than or equal to 0.001% by weight of unsaturated hydrocarbons, based on the sum of the hydrocarbons.

In a preferred embodiment, the inventive cosmetic and/or pharmaceutical formulations comprise hydrocarbon mixtures which comprise less than or equal to 20% by weight, especially less than or equal to 15% by weight, especially less than or equal to 10% by weight, preferably less than or equal to 9% by weight, preferably less than or equal to 8% by weight, preferably less than or equal to 5% by weight, of even-numbered hydrocarbons, based on the sum of the hydrocarbons.

These formulations can be obtained, for example, by using an inventive hydrocarbon mixture, or by using defined amounts of linear C11 and linear C13 hydrocarbons.

In a preferred embodiment, the cosmetic and/or pharmaceutical formulations comprise 10 to 60%, especially 5 to 50% and preferably 3 to 25% by weight of hydrocarbons, where the sum of the linear C11 and linear C13 hydrocarbons is greater than or equal to 60% by weight, based on the sum of the hydrocarbons.

Particular preference is given to cosmetic and/or pharmaceutical formulations comprising 0.1 to 80% by weight of hydrocarbons, wherein the hydrocarbons comprise 50 to 90% by weight of linear C11 hydrocarbons, preferably n-undecane to 50% by weight of linear C13 hydrocarbons, preferably n-tridecane based on the sum of the hydrocarbons.

Particular preference is given to cosmetic and/or pharmaceutical formulations comprising 0.1 to 80% by weight of hydrocarbons, wherein the hydrocarbons comprise 55 to 80% by weight, especially 60 to 75% by weight, especially 65 to 70% by weight, of linear C11 hydrocarbons, preferably n-undecane 20 to 45% by weight, especially 24 to 40% by weight, especially 24 to 30% by weight, of linear C13 hydrocarbons, preferably n-tridecane based on the sum of the hydrocarbons.

Particular preference is given to cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 70% by weight, especially greater than or equal to 80% by weight, preferably greater than or equal to 90% by weight, more preferably greater than or equal to 95% by weight, especially greater than or equal to 99% by weight, based on the sum of the hydrocarbons. In one embodiment of the invention, the hydrocarbons of the cosmetic and/or pharmaceutical formulation consist exclusively of linear C11 and linear C13 hydrocarbons, especially of n-undecane and n-tridecane.

In a preferred embodiment of the invention, the weight ratio of linear C11 hydrocarbons to linear C13 hydrocarbons in the cosmetic and/or pharmaceutical formulations is 1.5 to 3.5.

A preferred embodiment of the invention relates to cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight based on the sum of the hydrocarbons and the sum of the branched hydrocarbons is less than or equal to 10% by weight, based on the sum of the hydrocarbons. Particular preference is given to cosmetic and/or pharmaceutical formulations in which the sum of the branched hydrocarbons is less than or equal to 8% by weight, especially less than or equal to 5% by weight, especially less than or equal to 3% by weight, preferably less than or equal to 2% by weight, based on the sum of the hydrocarbons. In a preferred embodiment of the invention, the sum of the branched hydrocarbons is less than or equal to 1% by weight, based on the sum of the hydrocarbons.

A preferred embodiment of the invention relates to cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and in which the linear C11 and/or linear C13 hydrocarbons are saturated hydrocarbons; preferably, both the linear C11 and the linear C13 hydrocarbons are a linear hydrocarbon (n-undecane and n-tridecane).

A preferred embodiment of the invention relates to cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and the proportion of C12 hydrocarbons is less than or equal to 10% by weight, especially less than or equal to 5% by weight, preferably less than or equal to 3% by weight, based on the sum of the hydrocarbons.

A preferred embodiment of the invention relates to cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and where the sum of the hydrocarbons having a carbon chain length of greater than or equal to 14 is less than or equal to 15% by weight, especially less than or equal to 10% by weight, especially less than or equal to 8% by weight, preferably less than or equal to 4% by weight, especially less than or equal to 2% by weight, based on the sum of the hydrocarbons.

A preferred embodiment of the invention relates to cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and the sum of the hydrocarbons having a carbon chain length of less than or equal to 10 is less than or equal to 3% by weight, especially less than or equal to 2% by weight, preferably less than or equal to 1.5% by weight, especially less than or equal to 1% by weight, based on the sum of the hydrocarbons.

In one embodiment of the invention, the inventive cosmetic and/or pharmaceutical formulations comprise C12 and C14 hydrocarbons, preferably in the same weight ratio relative to one another as the linear C11 hydrocarbons to the linear C13 hydrocarbons. In a preferred embodiment of the invention, both the weight ratio of linear C11 hydrocarbons to linear C13 hydrocarbons and the weight ratio of C12 to C14 hydrocarbons are 1.5 to 3.5.

One embodiment of the invention relates to cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and the hydrocarbons consist of hydrocarbons having 7 to 23 hydrocarbons, preferably 9 to 21 hydrocarbons, more preferably 11 to 17 hydrocarbons.

With the inventive hydrocarbon mixtures, light, stable cosmetic and/or pharmaceutical formulations are obtained, which is the case especially when the hydrocarbon mixtures are used together with antiperspirant/deodorant active ingredients.

The invention therefore relates to cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and at least one antiperspirant/deodorant active ingredient.

According to the invention, suitable antiperspirant/deodorant active ingredients are all active ingredients which counteract, mask or eliminate body odors. Body odors arise as a result of the action of skin bacteria on apocrine perspiration, which forms unpleasant-smelling degradation products. Suitable antiperspirant/deodorant active ingredients are especially compounds selected from the group consisting of antiperspirants, esterase inhibitors, bactericidal or bacteriostatic active ingredients and/or perspiration-absorbing substances.
Antiperspirants Antiperspirants are salts of aluminum, of zirconium or of zinc. Such suitable antihydrotic active ingredients are, for example, aluminum chloride, aluminum chlorohydrate, aluminum dichlorohydrate, aluminum sesquichlorohydrate and complexes thereof, for example with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complexes thereof, for example with amino acids such as glycine. Preference is given to using aluminum chlorohydrate, aluminum zirconium tetrachlorohydrate, aluminum zirconium pentachlorohydrate and complexes thereof.

The inventive formulations may comprise the antiperspirants in amounts of 1 to 50%, preferably 5 to 30% and especially 8 to 25% by weight—based on the total weight of the cosmetic and/or pharmaceutical formulation.
Esterase Inhibitors In the presence of perspiration in the underarm region, bacteria form extracellular enzymes—esterases, preferably proteases and/or lipases—which cleave esters present in the perspiration and thus release odorants. Suitable esterase inhibitors are preferably trialkyl citrates such as trimethyl citrate, tripropyl citrate, triisopropyl citrate, tributyl citrate and especially triethyl citrate (Hydagen® CAT, Cognis GmbH, Düsseldorf/FRG). The substances inhibit enzyme activity and hence reduce odor formation. Further substances which are possible esterase inhibitors are sterol sulfates or phosphates, for example sulfates or phosphates of lanosterol, of cholesterol, of campesterol, of stigmasterol and of sitosterol, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

The inventive formulations may comprise the esterase inhibitors in amounts of 0.01 to 20%, preferably 0.1 to 10% and especially 0.3 to 5% by weight—based on the total weight of the cosmetic and/or pharmaceutical formulation.
Bactericidal or Bacteriostatic Active Ingredients Typical examples of suitable bactericidal or bacteriostatic active ingredients are especially chitosan and phenoxyethanol. 5-Chloro-2-(2,4-dichlorophenoxy)phenol has also been found to be particularly effective, and is sold under the Irgasan® brand by Ciba-Geigy, Basle, Switzerland. Suitable germicides are in principle all substances which act against Gram-positive bacteria, for example 4-hydroxybenzoic acid and the salts and esters thereof, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynylbutyl carbamate, chlorhexidine, 3,4,4'-trichlorocarbanilide (TTC), antibacterial odorants, thymol, thyme oil, eugenol, clove oil, menthol, mint oil, farnesol, phenoxyethanol, glyceryl monocaprate, glyceryl monocaprylate, glyceryl monolaurate (GML), diglyceryl monocaprate (DMC), N-alkylsalicylamides, for example n-octylsalicylamide or n-decylsalicylamide.

The inventive formulations may comprise the bactericidal or bacteriostatic active ingredients in amounts of 0.01 to 5% and preferably 0.1 to 2% by weight—based on the total weight of the cosmetic and/or pharmaceutical formulation.
Perspiration-absorbing Substances Useful perspiration-absorbing substances include modified starches, for example Dry Flo Plus (from National Starch), silicates, talc and other substances of similar polymorphism, which appear suitable for absorption of perspiration. The inventive formulations may comprise the perspiration-absorbing substances in amounts of 0.1 to 30%, preferably 1 to 20% and especially 2 to 8% by weight—based on the total weight of the cosmetic and/or pharmaceutical formulation.

With the inventive hydrocarbon mixtures, sensorily light, cosmetic and/or pharmaceutical formulations are obtained, which is the case especially when the hydrocarbon mixtures are used together with UV light protection filters.

The invention therefore provides cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and at least one UV light protection filter.

According to the invention, suitable UV light protection filters are room temperature liquid or crystalline organic substances (light protection filters) which are capable of absorbing ultraviolet rays and releasing the energy absorbed again in the form of longer-wave radiation, for example heat. UV filters may be oil-soluble or water-soluble. Examples of typical oil-soluble UV B filters or broad-spectrum UV A/B filters include:

3-benzylidenecamphor or 3-benzylidenenorcamphor (Mexoryl SDS 20) and derivatives thereof, e.g. 3-(4-methylbenzylidene)camphor as described in EP 0693471 B1

3-(4'-trimethylammonium)benzylidenebornan-2-one methylsulfate (Mexoryl SO)

3,3'-(1,4-phenylenedimethine)bis(7,7-dimethyl-2-oxobicyclo[2.2.1]heptane-1-methanesulfonic acid) and salts (Mexoryl SX)

3-(4'-sulfo)benzylidenebornan-2-one and salts (Mexoryl SL)

polymer of N-{(2 and 4)-[2-oxoborn-3-ylidene)-methyl}benzyl]acrylamide (Mexoryl SW)

2-(2H-benzotriazol-2-yl)-4-methyl-6-(2-methyl-3-(1,3,3,3-tetramethyl-1-(trimethylsilyloxy)-disiloxanyl)propyl)phenol (Mexoryl SL)

4-aminobenzoic acid derivatives, preferably 2-ethylhexyl 4-(dimethylamino)benzoate, 2-octyl 4-(dimethylamino)benzoate and amyl 4-(dimethyl-amino)benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homo-menthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethylhexyl 4-methoxybenzmalonate;

triazine derivatives, for example 2,4,6-trianilino(p-carbo-2'-ethyl-1'-hexyloxy)-1,3,5-triazine and 2,4,6-tris[p-(2-ethylhexyloxy-carbonyl)anilino]-1,3,5-triazine (Uvinul T 150), as described in EP 0818450 A1 or bis(2-ethylhexyl) 4,4'-[(6-[4-((1,1-dimethylethyl)aminocarbonyl)-phenylamino]-1,3,5-triazine-2,4-diyl)diimino]-benzoate (Uvasorb® HEB);

2,2-(methylenebis(6-(2H-benzotriazol-2-yl)-4-(1,1,3,3-tetramethylbutyl)phenol) (Tinosorb M);

2,4-bis[4-(2-ethylhexyloxy)-2-hydroxyphenyl]-6-(4-methoxyphenyl)-1,3,5-triazine (Tinosorb S); propane-1,3-diones, for example 1-(4-tert-butylphenyl)-3-(4'-methoxyphenyl)propane-1,3-dione;

ketotricyclo(5.2.1.0)decane derivatives, as described in EP 0694521 B1;

dimethicodiethyl benzalmalonates (Parsol SLX).

Useful water-soluble UV filters include:

2-phenylbenzimidazole-5-sulfonic acid and the alkali metal, alkaline earth metal, ammonium, alkylammonium, alkanolammonium and glucammonium salts thereof;

2,2-((1,4-phenylene)bis(1H-benzimidazole-4,6-disulfonic acid, monosodium salt) (Neo Heliopan AP);

sulfonic acid derivatives of benzophenones, preferably 2-hydroxy-4-methoxybenzophenone-5-sulfonic acid and its salts;

sulfonic acid derivatives of 3-benzylidenecamphor, for example 4-(2-oxo-3-bornylidenemethyl)benzene-sulfonic acid and 2-methyl-5-(2-oxo-3-bornylidene)sulfonic acid and salts thereof.

Useful typical UV A filters are especially derivatives of benzoylmethane, for example 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds, as described in DE 19712033 A1 (BASF), and also benzoic acid 2-[4-(diethylamino)-2-hydroxy-benzoyl]hexyl ester (Uvinul® A plus).

The UV A and UV B filters can of course also be used in mixtures. Particularly favorable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Combinations of this type are advantageously combined with water-soluble filters, for example 2-phenylbenzimidazole-5-sulfonic acid and the alkali metal, alkaline earth metal, ammonium, alkylammonium, alkanolammonium and glucammonium salts thereof.

Suitable UV light protection filters are especially the substances approved according to Annex VII of the Commission Directive (in the version Commission Directive 2005/9/EC of 28 Jan. 2005 amending Council Directive 76/768/EEC, concerning cosmetic products, for the purposes of adapting Annexes VII thereof to technical progress), to which reference is hereby explicitly made.

In addition to the soluble substances mentioned, insoluble light protection pigments, specifically finely dispersed metal oxides and salts, are also useful for this purpose. Examples of suitable metal oxides are especially zinc oxide and titanium dioxide, and additionally oxides of iron, of zirconium, of silicon, of manganese, of aluminum and of cerium, and mixtures thereof. The salts used may be silicates (talc), barium sulfate or zinc stearate. The oxides and salts are used in the form of the pigments for skincare and skin-protecting emulsions, and also for decorative cosmetics. The particles should have a mean diameter of less than 100 nm, preferably between 5 and 50 nm and especially between 15 and 30 nm. They may have a spherical shape, but it is also possible to use those particles which have an ellipsoidal shape or a shape which deviates in some other way from the spherical configuration. The pigments may also be present in surface-treated form, i.e. hydrophilized or hydrophobized. Typical examples thereof are coated titanium dioxides, for example T 805 titanium dioxide (Degussa) or Eusolex® T, Eusolex® T-2000, Eusolex® T-Aqua, Eusolex® AVO, Eusolex® T-ECO, Eusolex® T-OLEO and Eusolex® T-S (Merck). Typical examples are zinc oxides, for example Zinc Oxide neutral, Zinc Oxide NDM (Symrise) or Z-Cote® (BASF) or SUNZnO-AS and SUNZnO-NAS (Sunjun Chemical Co. Ltd.). Suitable hydrophobic coatings are in particular silicones and specifically trialkoxyoctylsilanes or simethicone. In sunscreen compositions, preference is given to using micropigments or nanopigments. Preference is given to using micronized zinc oxide. Further suitable UV light protection filters can be found in the review by P. Finkel in SÖFW Journal 122, 8/1996, pp. 543-548 and Parf. Kosm. 80th volume, no. 3/1999, p. 10 to 16.

In addition to the two aforementioned groups of primary light protection substances, it is also possible to use secondary light protection agents of the antioxidant type, which interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to mol/kg), also (metal) chelating agents (e.g. α-hydroxy fatty acids, palmitic acid, phytic acid, lactoferrin), α-hydroxy acids (e.g. citric acid, lactic acid, malic acid), humic acid, gallic acid, bile extracts, bilirubin, biliverdin, EDTA, EGTA and derivatives thereof, unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO4), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids), suitable in accordance with the invention, of these specified active ingredients.

A preferred embodiment of the invention relates to cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and at least one UV light protection filter selected from the group consisting of 4-methylbenzylidenecamphor, benzophenone-3, butyl-methoxydibenzoylmethane, bis-ethylhexyloxyphenol methoxyphenyl triazine, methylene bis-benzotriazolyl tetramethylbutylphenol, diethylhexyl butamido triazone, ethylhexyl triazone and diethylamino hydroxybenzoyl hexyl benzoate, 3-(4'-trimethylammonium)benzylidene-bornan-2-one methylsulfate, 3,3'-(1,4-phenylene-dimethine)bis(7,7-dimethyl-2-oxobicyclo[2.2.1]heptane-1-methanesulfonic acid) and its salts, 3-(4'-sulfo)-benzylidenebornan-2-one and its salts, polymer of N-{(2 and 4)-[2-oxoborn-3-ylidene)methyl}benzyl]acrylamide, 2-(2H-benzotriazol-2-yl)-4-methyl-6-(2-methyl-3-(1,3,3,3-tetramethyl-1-(trimethylsilyloxy)disiloxanyl)-propyl)phenol, dimethicodiethyl benzalmalonate and mixtures thereof.

These UV light protection filters are commercially available, for example, under the following trade names:

NeoHeliopan®MBC (INCI: 4-Methylbenzylidene Camphor; manufacturer: Symrise); NeoHeliopan®BB (INCI: Benzophenone-3, manufacturer: Symrise); Parsol®1789 (INCI: Butyl Methoxydibenzoylmethane, manufacturer: Hoffmann-La Roche (Givaudan)); Tinosorb®S (INCI: Bis-Ethylhexyloxyphenol Methoxyphenyl Triazine); Tinosorb®M (INCI: Methylene Bis-Benzotriazolyl Tetramethylbutyl-phenol): manufacturer: Ciba Specialty Chemicals Corporation; Uvasorb®HEB (INCI: Diethylhexyl Butamido Triazone, manufacturer: 3V Inc.), Uvinul®T 150 (INCI: Ethylhexyl Triazone, manufacturer: BASF AG); Uvinul® A plus (INCI: Diethylamino BASF Hydroxybenzoyl Hexyl Benzoate: manufacturer: Mexoryl® SO: 3-(4'-trimethylammonium)benzylidenebornan-2-one methylsulfate, INCI: Camphor Benzalkonium Methosulfate; Mexoryl®SX: 3,3'-(1,4-phenylenedimethine)bis(7,7-dimethyl-2-oxobicyclo[2.2.1]heptane-1-methanesulfonic acid), CTFA: INCI Terephthalylidene Dicamphor Sulfonic Acid; Mexoryl® SL: 3-(4'-sulfo)benzylidenebornan-2-one, INCI Benzylidene Camphor Sulfonic Acid; Mexoryl®SW: polymer of N-{(2 and 4)-[2-oxoborn-3-ylidene)methyl}-benzyl]acrylamide, INCI Polyacrylamidomethyl Benzylidene Camphor; Mexoryl®SL: 2-(2H-benzotriazol-2-yl)-4-methyl-6-(2-methyl-3-(1,3,3,3-tetramethyl-1-(trimethylsilyloxy)disiloxanyl)propyl)phenol; INCI: DROMETRIZOLE TRISILOXANE; Parsol® SLX: dimethicodiethyl benzalmalonate, INCI Polysilicone-15.

The inventive formulations may comprise the UV light protection filters in amounts of 0.5 to 30% by weight, preferably 2.5 to 20% by weight, more preferably 5-15% by weight—based on the total weight of the cosmetic and/or pharmaceutical formulation.

The invention provides cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and at least one self-tanning agent.

Self-tanning agents are understood to mean substances which cause browning of the skin. Examples include dihydroxyacetone, erythrulose and alpha, beta-unsaturated aldehydes, which react with the amino acids in the skin in the manner of a Maillard reaction to give colored compounds. Useful active ingredients for self-tanning agents also include natural or synthetic ketols or aldols. Examples of suitable active ingredients include dihydroxyacetone, erythrulose, glycerolaldehyde, alloxan, hydroxymethylglyoxal, gamma-dialdehyde, 6-aldo-D-fructose, ninhydrin and meso-tartaraldehyde. Suitable self-tanning agents are especially dihydroxyacetone and/or erythrulose.

Mixtures of the abovementioned active ingredients with one another or with muconaldehyde and/or naphthoquinones, for example 5-hydroxy-1,4-naphthoquinone (juglone) and 2-hydroxy-1,4-naphthoquinone, have been found to be particularly advantageous.

The inventive formulations comprise the self-tanning agents typically in concentrations of 1 to 10% and especially of 2 to 5% by weight—based on the total weight of the cosmetic and/or pharmaceutical formulation.

A particularly preferred embodiment of the invention relates to cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and at least one UV light protection filter and at least one self-tanning agent.

The inventive cosmetic and/or pharmaceutical formulations may be present, for example, as O/W or W/O care emulsions, sunscreen formulations, antiperspirant/deodorant concepts, formulations for decorative cosmetics, oily care formulations, impregnation liquids for substrates, for example paper and nonwoven products. Examples include wet wipes, tissues, diapers or hygiene products.

The inventive hydrocarbon mixtures and the inventive cosmetic and/or pharmaceutical formulations are especially also suitable for light, sprayable applications and/or as constituents of care emulsions for tissues, papers, wipes, sponges (e.g. polyurethane sponges), plasters in the baby hygiene sector, babycare, skincare, sun protection, aftersun treatment, insect repellency, cleansing, face cleansing and antiperspirant/deodorant applications. They can be applied to tissues, papers, wipes, nonwoven products, sponges, puffs, plasters and bandages which find use in the cleansing, hygiene and/or care sectors (wet wipes for baby hygiene and babycare, cleansing wipes, face cleansing wipes, skincare wipes, care wipes with active ingredients to counteract skin aging, wipes with sunscreen formulations and insect repellents, and wipes for decorative cosmetics or for aftersun treatment, toilet wet wipes, antiperspirant wipes, diapers, tissues, wet wipes, hygiene products, self-tanning wipes, toilet paper, refreshing wipes, aftershave wipes). They can also be used, inter alia, in formulations for hair care, hair cleaning or hair coloring. The use of the inventive hydrocarbon mixtures positively influences the sensory performance on application.

The inventive hydrocarbon mixtures are suitable especially as constituents of decorative cosmetics formulations, for example lipsticks, eye makeup, for example eyeshadow, mascara, eye pencils, kohl, nail varnish, etc., and makeup formulations.

The invention therefore provides cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and at least one pigment and/or dye.

The term pigment encompasses particles of any kind which are white or colored, organic or inorganic, are insoluble in the formulations, and serve the purpose of coloring the formulation.

In a preferred embodiment, inorganic pigments are used, particular preference being given to metal oxides.

Examples of inorganic pigments include: titanium dioxide, optionally surface-coated, zirconium or cerium oxides, and zinc, iron (black, yellow or red) and chromium oxides, manganese violet, ultramarine blue, chrome hydrates and iron(III) blue, metal powders such as aluminum powder or copper powder.

In a preferred embodiment of the invention, the pigment is selected from the inorganic pigments, preferably from the metal oxides. In a preferred embodiment, the pigment is selected from the group consisting of titanium dioxide, zinc oxide, iron oxide and mixtures thereof.

The pigments may be present either individually or in mixtures.

Preference is given in the context of the present invention to pigment mixtures composed of white pigments (e.g. kaolin, titanium dioxide or zinc oxide) and inorganic color pigments (e.g. iron oxide pigments, chromium oxides), and the pigments may be present in coated or uncoated form. Among the color pigments, iron oxides are particularly preferred.

Advantageously in the context of the present invention, the pigment(s) may also be selected from the group of the effect pigments which impart to the cosmetic formulation, in addition to the pure color, an additional property—for example angular dependence of the color (flop), luster (not surface luster) or texture. Such effect pigments are used in accordance with the invention advantageously in addition to one or more white and/or color pigments.

The most important group of the effect pigments is that of the luster pigments, which, according to DIN 55944: 2003-11, include the metal effect pigments and the pearlescent pigments. Some specific effect pigments cannot be assigned to these two groups, for example graphite platelets, iron oxide platelets and micronized titanium dioxide, the latter not giving a luster effect, but rather an angle-dependent light-scattering effect. The luster pigments to DIN 55943: 2001-10 are predominantly effect pigment platelets. Aligned in parallel, luster pigments exhibit a characteristic luster. The visual effect of luster pigments is based on the directed reflection on metallic particles (metal effect pigments), on transparent particles with a high refractive index (pearlescent pigments) or on the phenomenon of interference (interference pigments) (DIN 55944: 2003-11).

Examples of commercial effect pigments preferred in accordance with the invention are: Timiron and #174; from Merck, Iriodin and #174; from Merck (pearlescent and color luster pigments for decorative industrial applications), Xirallic and #174; from Merck (intense-color crystal effect pigments).

In addition, the inventive formulations may advantageously also comprise organic color pigments, i.e. organic dyes which are virtually insoluble in the formulation. According to DIN 55944: 1990-04, organic pigments can be divided according to chemical aspects into azo pigments and polycyclic pigments, and according to color aspects into chromatic or black pigments. Organic white pigments are of no practical significance.

In the context of the present invention, the pigments can advantageously also be employed in the form of commercially available oily or aqueous predispersions. The inventive formulations comprise typically 0.1 to 40% by weight of pigments—based on the total weight of the cosmetic and/or pharmaceutical formulation.

It is also advantageous in the context of the present invention when the inventive formulation comprises one or more dyes.

The dyes may be either of synthetic or natural origin. A list of suitable dyes can be found in EP 1 371 359 A2, page 8, lines 25-57, page 9 and page 10, and also page 11, lines 1 to 54, to which reference is hereby explicitly made.

The inventive formulations comprise typically 0.01 to 5% and preferably 0.1 to 1.0% by weight of dyes—based on the total weight of the cosmetic and/or pharmaceutical formulation. The inventive formulations typically comprise a total amount of dyes and pigments in the range from 0.01 to 30% by weight, especially 0.1 to 15% by weight, preferably 1 to 10% by weight, based on the total weight of the cosmetic and/or pharmaceutical formulation.

Suitable dyes and pigments are especially the dyes and pigments approved according to Annex IV of the Commission Directive (in the version: Commission Directive 2007/22/EC of 17 Apr. 2007 amending Council Directive 76/768/EEC, concerning cosmetic products, for the purposes of adapting Annexes IV and VI thereto to technical progress), to which reference is hereby explicitly made.

The cosmetic and/or pharmaceutical formulations may be formulations for bodycare, for example a body milk, creams, lotions, sprayable emulsions, products for eliminating body odor, etc. The hydrocarbon mixtures can also be used in surfactant-containing formulations, for example shower and bath gels, shampoos and care rinses. According to the end application, the cosmetic and/or pharmaceutical formulations comprise a series of further assistants and additives, for example surfactants, further oil bodies, emulsifiers, pearlescent waxes, bodying agents, thickeners, superfatting agents, stabilizers, polymers, fats, waxes, lecithins, phospholipids, biogenic active ingredients, antidandruff agents, film formers, swelling agents, insect repellents, self-tanning agents, tyrosinase inhibitors (depigmenting agents), hydrotropes, solubilizers, preservatives, perfume oils, dyes, etc., which are listed below by way of example.

The invention further provides cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and at least one emulsifier and/or a surfactant and/or a wax component and/or a polymer and/or a further oil body.

Emulsifier

In one embodiment of the invention, the inventive formulations comprise at least one emulsifier.

The invention therefore further provides cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and at least one emulsifier.

The inventive formulations comprise the emulsifier(s) typically in an amount of 0 to 40% by weight, preferably 0.1 to 20% by weight, preferably 0.1 to 15% by weight and especially 0.1 to 10% by weight, based on the total weight of the formulation.

Every emulsifier is assigned a so-called HLB value (a dimensionless number between 0 and 20) which specifies whether there is a preference for water or oil solubility. Numbers below 9 indicate preferentially oil-soluble, hydrophobic emulsifiers, numbers above 11 water-soluble, hydrophilic emulsifiers. The HLB value says something about the equilibrium of the size and strength of the hydrophilic and lipophilic groups of an emulsifier. The HLB value of an emulsifier can also be calculated from increments, and the HLB increments for the different hydrophilic and hydrophobic groups from which a molecule is composed can be found in tabular works (e.g. H. P. Fiedler, Lexikon der Hilfsstoffe für Pharmazie, Kosmetik and angrenzende Gebiete [Lexicon of the Excipients for Pharmacy, Cosmetics and Related Fields], Editio Cantor Verlag, Aulendorf, 4th Ed. 1996) or manufacturer data. The solubility of the emulsifier in the two phases effectively determines the emulsion type. When the emulsifier has better solubility in water, an O/W emulsion is obtained. When the emulsifier, in contrast, has better solubility in the oil phase, a W/O emulsion arises under otherwise identical production conditions.

In one embodiment of the invention, the inventive formulation comprises more than one emulsifier.

Depending on the other components, the person skilled in the art uses customary emulsifier systems (for example emulsifier and coemulsifier).

Nonionic Emulsifiers

The group of nonionic emulsifiers includes, for example:
(1) Addition products of 2 to 50 mol of ethylene oxide and/or 1 to 20 mol of propylene oxide onto linear fatty alcohols having 8 to 40 carbon atoms, onto fatty acids having 12 to 40 carbon atoms and onto alkylphenols having 8 to 15 carbon atoms in the alkyl group.
(2) $C_{12}$-$C_{18}$ fatty acid mono- and diesters of addition products of 1 to 50 mol of ethylene oxide onto glycerol.
(3) Sorbitan mono- and diesters of saturated and unsaturated fatty acids having 6 to 22 carbon atoms and ethylene oxide addition products thereof.
(4) Alkyl mono- and oligoglycosides having 8 to 22 carbon atoms in the alkyl radical and ethoxylated analogs thereof.
(5) Addition products of 7 to 60 mol of ethylene oxide onto castor oil and/or hydrogenated castor oil.
(6) Polyol and especially polyglyceryl esters, for example polyol poly-12-hydroxystearates, polyglyceryl polyricinoleate, polyglyceryl diiso-stearate or polyglyceryl dimerate. Likewise suitable are mixtures of compounds of two or more of these substance classes.
(7) Addition products of 2 to 15 mol of ethylene oxide onto castor oil and/or hydrogenated castor oil.
(8) Partial esters based on linear, branched, unsaturated or saturated $C_6$-$C_{22}$-fatty acids, ricinoleic acid and 12-hydroxystearic acid and polyglycerol, pentaerythritol, dipentaerythritol, sugar alcohols (e.g. sorbitol), alkyl glucosides (e.g. methyl glucoside, butyl glucoside, lauryl glucoside) and polyglucosides (e.g. cellulose), or mixed esters, for example glyceryl stearate citrate and glyceryl stearate lactate.
(9) Polysiloxane-polyalkyl-polyether copolymers and corresponding derivatives.
(10) Mixed esters of pentaerythritol, fatty acids, citric acid and fatty alcohol and/or mixed esters of fatty acids having 6 to 22 carbon atoms, methylglucose and polyols, preferably glycerol or polyglycerol.

The addition products of ethylene oxide and/or of propylene oxide onto fatty alcohols, fatty acids, alkylphenols, glyceryl mono- and diesters and also sorbitan mono- and diesters of fatty acids and onto castor oil are known, commercially available products. These are homolog mixtures whose mean degree of alkoxylation corresponds to the ratio of the amounts of ethylene oxide and/or propylene oxide and substrate with which the addition reaction is carried out. Depending on the degree of ethoxylation, they are W/O or O/W emulsifiers. $C_{12/18}$ fatty acid mono- and diesters of addition products of ethylene oxide onto glycerol are known as refatting agents for cosmetic formulations.

Mild emulsifiers which are particularly suitable in accordance with the invention are polyol poly-12-hydroxystearates and mixtures thereof, which are sold, for example, under the "Dehymuls® PGPH" (W/O emulsifier) or "Eumulgin® VL 75" (blend with Lauryl Glucosides in a weight ratio of 1:1, O/W emulsifier) or Dehymuls® SBL (W/O emulsifier) brands by Cognis Deutschland GmbH. In this connection, reference may be made especially to European patent EP 766 661 B1. The polyol component of these emulsifiers may derive from substances which have at least two, preferably 3 to 12 and especially 3 to 8 hydroxyl groups and 2 to 12 carbon atoms.

Particularly preferred emulsifiers are, for example, Cetyl Dimethicone Copolyol (e.g. Abil EM-90), Polyglyceryl-2 Dipolyhydroxystearate (e.g. Dehymuls PGPH), Polyglyceryl-3 Diisostearate (e.g. Lameform TGI), Polyglyceryl-4 Isostearate (e.g. Isolan GI 34), Polyglyceryl-3 Oleate (e.g. Isolan GO 33), Diisostearoyl Polyglyceryl-3 Diisostearate (e.g. Isolan PDI), Polyglyceryl-3 Methylglucose Distearate (e.g. Tego Care 450), Polyglyceryl-3 Beeswax (e.g. Cera Bellina), Polyglyceryl-4 Caprate (e.g. Polyglycerol Caprate T2010/90), Polyglyceryl-3 Cetyl Ether (e.g. Chimexane NL), Polyglyceryl-3 Distearate (e.g. Cremophor GS 32) and Polyglyceryl Polyricinoleate (e.g. Admul WOL 1403), Glyceryl Oleate (e.g. Monomuls 90-O 18), Alkyl Glucoside (e.g. Plantacare 1200, Emulgade PL 68/50, Montanov 68, Tego Care CG 90, Tego Glucosid L 55), Methyl Glucose Isostearate (e.g. Tego Care IS), Methyl Glucose Sesquistearate (Tego Care PS), Sodium Cocoyl Hydrolyzed Wheat Protein (e.g. Gluadin WK), Potassium Cetyl Phosphate (e.g. Amphisol K, Crodafos CKP), Sodium Alkylsulfate (e.g. Lanette E), Sucrose Ester (e.g. Crodesta F-10, F-20, F-50, F-70, F-110, F-160, SL-40, Emulgade® Sucro), ethoxylated and/or propoxylated fatty alcohols, fatty acids, castor oils and hydrogenated castor oils (e.g. Eumulgin B2, B2, B3, L, HRE 40, HRE 60, RO 40, Cremophor HRE 40, HRE 60, L, WO 7, Dehymuls HRE 7, Arlacel 989), PEG-30 Dipolyhydroxystearate (e.g. Arlacel P 135, Dehymuls LE), sorbitan esters, sorbitan esters ethoxylated and/or propoxylated, and mixtures thereof. A particularly effective mixture consists of Polyglyceryl-2 Dipolyhydroxystearate and Lauryl Glucoside and glycerol (e.g. Eumulgin VL 75). Also suitable are Polyglyceryl-4 Diisostearate/Polyhydroxy-stearate/Sebacate (Isolan® GPS), Diisostearoyl Polyglyceryl-3 Diisostearate (e.g. Isolan PDI), alkali metal acylglutamates (e.g. Eumulgin SG).

Suitable lipophilic W/O emulsifiers are in principle emulsifiers with an HLB value of 1 to 8, which are summarized in numerous tabular works and are known to the person skilled in the art. Some of these emulsifiers are listed, for example, in Kirk-Othmer, "Encyclopedia of Chemical Technology", 3rd edition, 1979, volume 8, page 913. For ethoxylated products, the HLB value can also be calculated according to the following formula: HLB=(100−L):5, where L is the weight fraction of the lipophilic groups, i.e. of the fatty alkyl or fatty acyl groups in percent by weight, in the ethylene oxide adducts.

Particularly advantageous from the group of W/O emulsifiers are partial esters of polyols, especially of $C_4$-$C_6$-polyols, for example partial esters of pentaerythritol or sugar esters, e.g. sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxy-stearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical-grade mixtures thereof. Also suitable as emulsifiers are addition products of 1 to 30 and preferably 5 to 10 mol of ethylene oxide onto the specified sorbitan esters.

Depending on the formulation, it may be advantageous to additionally use at least one emulsifier from the group of nonionic O/W emulsifiers (HLB value: 8-18) and/or solubilizers. These are, for example, the ethylene oxide adducts already mentioned in the introduction and having a correspondingly high degree of ethoxylation, e.g. 10-20 ethylene oxide units for O/W emulsifiers and 20-40 ethylene oxide units for solubilizers. According to the invention, Ceteareth-12 and PEG-20 Stearate are particularly advantageous as O/W emulsifiers. Preferentially suitable solubilizers are Eumulgin® HRE 40 (INCI: PEG-40 Hydrogenated Castor Oil), Eumulgin® HRE 60 (INCI: PEG-60 Hydrogenated Castor Oil), Eumulgin® L (INCI: PPG-1-PEG-9 Lauryl Glycol Ether), and Eumulgin® SML 20 (INCI: Polysorbate-20).

Nonionic emulsifiers from the group of alkyl oligoglycosides are particularly skin-friendly and therefore preferentially suitable as O/W emulsifiers. $C_8$-$C_{22}$-alkyl mono- and oligoglycosides, their preparation and their use are known from the prior art. Their preparation takes place especially by reacting glucose or oligosaccharides with primary alcohols having 8 to 22 carbon atoms. As regards the glycoside radical, either monoglycosides, in which a cyclic sugar radical is glycosidically bonded to the fatty alcohol, or oligomeric glycosides with a degree of oligomerization up to preferably about 8 are suitable. The degree of oligomerization here is a statistical average based on a homolog distribution customary for such technical-grade products. Products which are available under the name Plantacare® comprise a glucosidically bonded $C_8$-$C_{16}$-alkyl group onto an oligoglucoside radical whose average degree of oligomerization is 1 to 2. The acylglucamides derived from glucamine are also suitable as nonionic emulsifiers. According to the invention, preference is given to a product which is sold under the name Emulgade® PL 68/50 by Cognis Deutschland GmbH and is a 1:1 mixture of alkyl polyglucosides and fatty alcohols. According to the invention, it is also advantageously possible to use a mixture of Lauryl Glucoside, Polyglyceryl-2 Dipolyhydroxystearate, glycerol and water, which is commercially available under the name Eumulgin® VL 75.

Also suitable as emulsifiers are substances such as lecithins and phospholipids. Examples of natural lecithins which may be mentioned are the cephalins, which are also referred to as phosphatidic acids and are derivatives of 1,2-diacyl-sn-glycerol-3-phosphoric acids. By contrast, phospholipids are usually understood to mean mono- and preferably diesters of phosphoric acid with glycerol (glycerol phosphates), which are generally included in the fats. In addition, sphingosines and sphingolipids are also suitable.

The emulsifiers present may, for example, be silicone emulsifiers. These may be selected, for example, from the group of alkylmethicone copolyols and/or alkyldimethicone copolyols, especially from the group of compounds which are characterized by the following chemical structure:

alkyl groups, acyl groups and alkoxy groups having 1-24 carbon atoms, p is 0-200, q is 1-40, and r is 1-100.

One example of silicone emulsifiers to be used particularly advantageously within the context of the present invention is that of dimethicone copolyols, which are sold by Evonik Goldschmidt under the trade names AXIL® B 8842, ABIL® B 8843, ABIL® B 8847, ABIL® B 8851, ABIL® B 8852, ABIL® B 8863, ABIL® B 8873 and ABIL® B 88183. A further example of interface-active substances to be used particularly advantageously within the context of the present invention is that of cetyl PEG/PPG-10/1 dimethicone (cetyl dimethicone copolyol), which is sold by Evonik Goldschmidt under the trade name ABIL® EM 90. A further example of interface-active substances to be used particularly advantageously within the context of the present invention is that of cyclomethicone dimethicone copolyol, which is sold by Evonik Goldschmidt under the trade name ABIL® EM 97 and ABIL® WE 09. In addition, the emulsifier lauryl PEG/PPG-18/18 methicone (laurylmethicone copolyol) has been found to be very particularly advantageous and is available under the trade name Dow Corning® 5200 Formulation Aid from Dow Corning Ltd. A further advantageous silicone emulsifier is octyl dimethicone ethoxy glucoside from Wacker. For an inventive water-in-silicone oil emulsion, all known emulsifiers used for this type of emulsion can be used. Water-in-silicone emulsifiers which are particularly preferred in accordance with the invention are cetyl PEG/PPG-10/1 dimethicone and lauryl PEG/PPG-18/18 methicone [e.g. ABIL® EM 90 (Evonik Goldschmidt), DC5200 Formulation Aid (Dow Corning)] and any desired mixtures of the two emulsifiers.

Surfactants

In one embodiment of the invention, the inventive formulations comprise at least one surfactant.

Surfactants are amphiphilic substances which can dissolve organic, nonpolar substances in water. They cause, as a result of their specific molecular structure with at least one hydrophilic and a hydrophobic molecular moiety, a lowering of the surface tension of the water, the wetting of the skin, the facilitation of soil removal and dissolution, easy rinseoff and—if desired—foam regulation.

Surfactants are typically understood to mean surface-active substances which have an HLB value of greater than 20.

The invention therefore further provides cosmetic and/or pharmaceutical formulations comprising 0.1 to 80% by weight of hydrocarbons which comprise linear C11 and linear C13 hydrocarbons, where the sum of the linear C11 and the linear C13 hydrocarbons is greater than or equal to 60% by weight, based on the sum of the hydrocarbons, and at least one surfactant.

The surface-active substances present may be anionic, nonionic, cationic and/or amphoteric or zwitterionic surfactants. In surfactant-containing cosmetic formulations, for

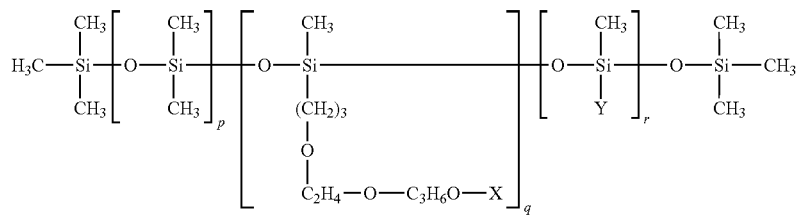

in which X and Y are each independently selected from the group of H (hydrogen) and the branched and unbranched example shower gels, foam baths, shampoos, etc., at least one anionic surfactant is preferably present.

The inventive formulations comprise the surfactant(s) typically in an amount of 0 to 40% by weight, preferably 0.05 to 30% by weight, especially 0.05 to 20% by weight, preferably 0.1 to 15% by weight and especially 0.1 to 10% by weight, based on the total weight of the formulation.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucuronic acid derivatives, fatty acid N-alkylglucamides, protein hydrolyzates (especially wheat-based vegetable products), polyol fatty acid esters, sugar esters, sorbitan esters, polysorbates and amine oxides. If the nonionic surfactants contain polyglycol ether chains, they may have a conventional homolog distribution, but preferably have a narrow homolog distribution.

Zwitterionic surfactants refer to those surface-active compounds which bear at least one quaternary ammonium group and at least one —COO$^{(-)}$ or —SO$_3^{(-)}$ group in the molecule. Particularly suitable zwitterionic surfactants are the betaines, such as the N-alkyl-N,N-dimethylammonium glycinates, for example cocoalkyl dimethylammonium glycinate, N-acylaminopropyl-N,N-dimethylammonium glycinates, for example cocoacylamino-propyldimethylammonium glycinate, and 2-alkyl-3-carboxymethyl-3-hydroxyethylimidazoline having in each case 8 to 18 carbon atoms in the alkyl or acyl group, and also cocoacylaminoethyl hydroxyethylcarboxymethyl glycinate. A preferred zwitterionic surfactant is the fatty acid amide derivative known under the INCI name Cocamidopropyl Betaine.

Likewise suitable, especially as cosurfactants, are ampholytic surfactants. Ampholytic surfactants are understood to mean those surface-active compounds which, apart from a $C_8$-$C_{18}$-alkyl or acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkylimino-dipropionic acids, N-hydroxyethyl-N-alkylamidopropyl-glycines, N-alkyltaurines, N-alkylsarcosines, 2-alkyl-aminopropionic acids and alkylaminoacetic acids having in each case about 8 to 18 carbon atoms in the alkyl group. Particularly preferred ampholytic surfactants are N-cocoalkylaminopropionate, cocoacylaminoethyl-amino-propionate and $C_{12-18}$-acylsarcosine.

Typical examples of amphoteric or zwitterionic surfactants are alkylbetaines, alkylamidobetaines, aminopropionates, aminoglycinates, imidazolinium betaines and sulfobetaines. The specified surfactants are exclusively known compounds. With regard to the structure and preparation of these substances, reference may be made to relevant review works in this field. Typical examples of particularly suitable mild, i.e. particularly skin-friendly, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides and/or mixtures thereof with alkyl oligoglucoside carboxylates, fatty acid glucamides, alkylamidobetaines, amphoacetals and/or protein fatty acid condensates, the latter preferably based on wheat proteins or salts thereof.

Anionic surfactants are characterized by a water-solubilizing, anionic group, for example a carboxylate, sulfate, sulfonate or phosphate group and a lipophilic radical. Skin-compatible anionic surfactants are known to the person skilled in the art in a large number from relevant handbooks and are commercially available. These are especially alkyl sulfates in the form of their alkali metal, ammonium or alkanolammonium salts, alkyl ether sulfates, alkyl ether carboxylates, acyl isethionates, acyl sarcosinates, acyltaurines with linear alkyl or acyl groups having 12 to 18 carbon atoms, and also sulfosuccinates and acyl glutamates in the form of their alkali metal or ammonium salts.

Typical examples of anionic surfactants are soaps, alkylbenzenesulfonates, alkanesulfonates, olefin-sulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ethercarboxylic acids and salts thereof, fatty acid isethionates, fatty acid sarcosinates, fatty acid taurides, N-acylamino acids, for example acyl lactylates, acyl tartrates, acyl glutamates and acyl aspartates, alkyl oligoglucoside sulfates, protein fatty acid condensates (especially vegetable products based on wheat) and alkyl (ether) phosphates. If the anionic surfactants comprise polyglycol ether chains, these may have a conventional homolog distribution, but preferably have a narrow homolog distribution.

Cationic surfactants which can be used are especially quaternary ammonium compounds. Preference is given to ammonium halides, especially chlorides and bromides, such as alkyltrimethylammonium chlorides, dialkyldimethylammonium chlorides and trialkylmethyl-ammonium chlorides, e.g. cetyltrimethylammonium chloride, stearyltrimethylammonium chloride, distearyl-dimethylammonium chloride, lauryldimethylammonium chloride, lauryldimethylbenzylammonium chloride and tricetylmethylammonium chloride. In addition, the very readily biodegradable quaternary ester compounds, for example the dialkylammonium methosulfates and methylhydroxyalkyldialkyloxyalkylammonium methosulfates sold under the trade name Stepantex® and the corresponding products of the Dehyquart® series can also be used as cationic surfactants. The term "ester quats" are generally understood to mean quaternized fatty acid triethanolamine ester salts. They can impart an exceptional soft feel to the preparations according to the invention. These are known substances which are prepared by the relevant methods of organic chemistry. Further cationic surfactants which can be used in accordance with the invention are the quaternized protein hydrolyzates.

Wax Component

In one embodiment of the invention, the inventive formulations comprise at least one wax component.

The invention therefore further relates to cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and at least one wax component.

The inventive formulations comprise the wax component(s) typically in an amount of 0 to 40% by weight, especially of 0 to 20% by weight, preferably 0.1 to 15% by weight and especially 0.1 to 10% by weight, based on the total weight of the formulation. The term "wax" is typically understood to mean all natural or synthetic substances and substance mixtures having the following properties: they are of solid to brittle and hard consistency, coarse to finely crystalline, transparent to cloudy and melt above 30° C. without decomposition. They are low in viscosity even a little above the melting point and do not string, and exhibit a strongly temperature-dependent consistency and solubility. According to the invention, it is possible to use a wax component or a mixture of wax components which melt at 30° C. or higher.

The waxes used in accordance with the invention may also be fats and fat-like substances with waxy consistency, provided they have the required melting point. These include, inter alia, fats (triglycerides), mono- and diglycerides, natural and synthetic waxes, fatty and wax alcohols, fatty acids, esters of fatty alcohols and fatty acids and also fatty acid amides or any desired mixtures of these substances.

Fats are understood to mean triacylglycerols, i.e. the triple esters of fatty acids with glycerol. They preferably comprise saturated, unbranched and unsubstituted fatty acid radicals. They may also be mixed esters, i.e. triple esters of glycerol with different fatty acids. According to the invention, it is possible to use hydrogenated fats and oils, which are obtained by partial hydrogenation and are particularly suitable as consistency regulators. Vegetable hydrogenated fats and oils are preferred, e.g. hydrogenated castor oil, peanut oil, soybean oil, rapeseed oil, colza oil, cottonseed oil, soybean oil, sunflower oil, palm oil, palm kernel oil, linseed oil, almond oil, corn oil, olive oil, sesame oil, cocoa butter and coconut fat.

Suitable examples include the triple esters of glycerol with C12-C60-fatty acids and especially C12-C36-fatty acids. These include hydrogenated castor oil, a triple ester of glycerol and a hydroxystearic acid, which is commercially available, for example, under the Cutina HR name. Glyceryl tristearate, glyceryl tribehenate (e.g. Syncrowax HRC), glyceryl tripalmitate or the triglyceride mixtures known under the Syncrowax HGLC name are likewise suitable, with the proviso that the melting point of the wax component or of the mixture is 30° C. or higher.

According to the invention, usable wax components are especially mono- and diglycerides and mixtures of these partial glycerides. Glyceride mixtures which can be used in accordance with the invention include the Novata AB and Novata B (mixture of C12-C18-mono-, di- and triglycerides) and Cutina MD or Cutina GMS (glyceryl stearate) products sold by Cognis Deutschland GmbH & Co. KG.

Fatty alcohols which can be used in accordance with the invention as the wax component include the C12-050-fatty alcohols. The fatty alcohols can be obtained from natural fats, oils and waxes, for example myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. Preference is given in accordance with the invention to saturated unbranched fatty alcohols. However, it is also possible in accordance with the invention to use unsaturated, branched or unbranched fatty alcohols as the wax component, provided they have the required melting point. It is also possible in accordance with the invention to use fatty alcohol cuts, as produced in the reduction of naturally occurring fats and oils, for example bovine tallow, peanut oil, colza oil, cottonseed oil, soybean oil, sunflower oil, palm kernel oil, linseed oil, castor oil, corn oil, rapeseed oil, sesame oil, cocoa butter and coconut fat. However, it is also possible to use synthetic alcohols, e.g. the linear, even-numbered fatty alcohols from the Ziegler synthesis (alfols) or the partially branched alcohols from the oxo process (dobanols). Particular preference is given in accordance with the invention to C14-C22-fatty alcohols, which are sold, for example, by Cognis Deutschland GmbH under the Lanette 18 (C18-alcohol), Lanette 16 (C16-alcohol), Lanette 14 (C14-alcohol), Lanette 0 (C16/C18-alcohol) and Lanette 22 (C18/C22-alcohol) names. Fatty alcohols impart a drier skinfeel to the formulations than triglycerides and are therefore preferred over the latter.

The wax components used may also be C14-C40-fatty acids or mixtures thereof. These include, for example, myristic acid, pentadecanoic acid, palmitic acid, margaric acid, stearic acid, nonadecanoic acid, arachic acid, behenic acid, lignoceric acid, cerotic acid, melissic acid, erucic acid and elaeostearic acid, and also substituted fatty acids, for example 12-hydroxystearic acid, and the amides or monoethanolamides of the fatty acids, this list being illustrative and non-limiting in character.

It is possible in accordance with the invention to use, for example, natural vegetable waxes, such as candelilla wax, carnauba wax, japan wax, esparto grass wax, cork wax, guaruma wax, rice germ wax, sugarcane wax, ouricury wax, montan wax, sunflower wax, fruit waxes such as orange waxes, lemon waxes, grapefruit wax, bayberry wax, and animal waxes, for example beeswax, shellac wax, spermaceti, wool wax and uropygial grease. In the context of the invention, it may be advantageous to use hydrogenated or hardened waxes. The natural waxes which can be used in accordance with the invention also include mineral waxes, for example ceresin and ozokerite or the petrochemical waxes, for example petrolatum, paraffin waxes and microwaxes. Usable wax components also include chemically modified waxes, especially the hard waxes, for example montan ester waxes, sasol waxes and hydrogenated jojoba waxes. Synthetic waxes which can be used in accordance with the invention include, for example, wax-like polyalkylene waxes and polyethylene glycol waxes. Vegetable waxes are preferred in accordance with the invention.

The wax component can likewise be selected from the group of the wax esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (e.g. 12-hydroxystearic acid) and saturated and/or unsaturated, branched and/or unbranched alcohols, and also from the group of lactides of long-chain hydroxycarboxylic acids. Examples of such esters are the C16-C40-alkyl stearates, C20-C40-alkyl stearates (e.g. Kesterwachs K82H), C20-C40-dialkyl esters of dimeric acids, C18-C38-alkylhydroxystearoyl stearates or C20-C40-alkyl erucates. It is also possible to use C30-050-alkylbeeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate. Fatty acid partial glycerides, i.e. technical-grade mono- and/or diesters of glycerol with fatty acids having 12 to 18 carbon atoms, for example glycerol mono/dilaurate, -palmitate, -myristate or -stearate, are also useful for this purpose.

Suitable waxes are additionally pearlescent waxes. Useful pearlescent waxes, especially for use in surface-active formulations, are, for example: alkylene glycol esters, especially ethylene glycol distearate; fatty acid alkanolamides, especially coconut fatty acid diethanolamide; partial glycerides, especially stearic acid monoglyceride; esters of polybasic, optionally hydroxy-substituted carboxylic acids with fatty alcohols having 6 to 22 carbon atoms, especially long-chain esters of tartaric acid; fatty substances, for example fatty alcohols, fatty ketones, fatty aldehydes, fatty ethers and fatty carbonates, which have a total of at least 24 carbon atoms, especially laurone and distearyl ethers; fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Polymers

In one embodiment of the invention, the inventive formulations comprise at least one polymer.

The invention therefore further provides cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and at least one polymer.

The inventive formulations comprise the polymer(s) typically in an amount of 0 to 20% by weight, preferably 0.1 to 15% by weight and especially 0.1 to 10% by weight, based on the total weight of the formulation.

Suitable cationic polymers are, for example, cationic cellulose derivatives, for example a quaternized hydroxyethylcellulose, which is available under the Polymer JR 400® name from Amerchol, cationic starch, copolymers of diallylammonium salts and acrylamides, quaternized vinylpyrrolidone/vinylimidazole polymers, for example Luviquat® (BASF), condensation products of polyglycols and amines, quaternized collagen polypeptides, for example lauryldimonium hydroxypropyl hydrolyzed collagen (Lamequat®L/Grünau), quaternized wheat polypeptides, polyethyleneimine, cationic silicone polymers, for example amidomethicones, copolymers of adipic acid and dimethylaminohydroxypropyldiethylenetriamine (Cartaretine®/Sandoz), copolymers of acrylic acid with dimethyldiallylammonium chloride (Merquat® 550/Chemviron), polyaminopolyamides, cationic chitin derivatives for example quaternized chitosan, optionally in microcrystalline distribution, condensation products of dihaloalkylene, for example dibromobutane with bisdialkylamines, for example bisdimethylamino-1,3-propane, cationic guar gum, for example Jaguar® CBS, Jaguar® C-17, Jaguar® C-16 from Celanese, quaternized ammonium salt polymers, for example Mirapol® A-15, Mirapol® AD-1, Mirapol® AZ-1 from Miranol.

Useful anionic, zwitterionic, amphoteric and nonionic polymers are, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octylacrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinylcaprolactam terpolymers and optionally derivatized cellulose ethers and silicones.

Likewise suitable polymers are polysaccharides, in particular xanthan gum, guar guar, agar agar, alginates and tyloses and also, for example, Aerosil grades (hydrophilic silicas), carboxymethylcellulose and hydroxyethylcellulose and hydroxypropylcellulose, poly-vinyl alcohol, polyvinylpyrrolidone and bentonites, for example Bentone® Gel VS-5PC (Rheox).

Likewise suitable are quaternary polymers, for example with the INCI name Polyquaternium-37, which conform to the following general formula:

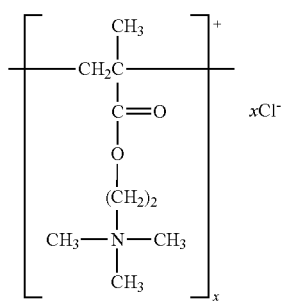

Alternatively, it is also possible to use other dialkylaminoalkyl (meth)acrylates and their ammonium salts obtainable by alkylation or protonation, or dialkylaminoalkyl(meth)acrylamides and their ammonium salts obtainable by alkylation or protonation. Particular preference is given to polymers comprising MAPTAC, APTAC, MADAME, ADAME, DMAEMA and TMAEMAC. Moreover, it is also possible to use copolymers with anionic, further cationic or uncharged monomers in accordance with the invention, in particular those which, as well as the specified alkylaminoalkyl (meth)acrylate or alkylaminoalkyl(meth)acrylamide monomers, additionally comprise (meth)acrylic acid and/or 2-acrylamido-2-methylpropanesulfonic acid and/or acrylamide and/or vinylpyrrolidone and/or alkyl (meth)-acrylates. By way of example, mention may be made of those polymers with the INCI name Polyquaternium-11, Polyquaternium-13, Polyquaternium-14, Polyquaternium-15, Polyquaternium-28, Polyquaternium-32, Polyquaternium-43, Polyquaternium-47.

Oil Bodies

In one embodiment of the invention, the inventive formulations comprise at least one oil body. Typically, the inventive formulations comprise the hydrocarbon mixture as the oil body. In the embodiment specified here as preferred, the formulations thus comprise an oil body other than the inventive hydrocarbon mixture, also referred to as "further oil body".

The invention therefore further provides cosmetic and/or pharmaceutical formulations comprising 1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and at least one (further) oil body.

The oil bodies (inventive hydrocarbon mixture plus further oil bodies) are typically present in a total amount of 0.1-90%, especially 0.1-80%, especially 0.5 to 70%, preferably 1 to 60%, especially 1 to 50%, especially 1 to 40%, preferably 5-25% and especially 5-15% by weight. The further oil bodies are typically present in an amount of 0.1 to 40% by weight, based on the total weight of the formulation.

Suitable further oil bodies are, for example, Guerbet alcohols based on fatty alcohols having 6 to 18, preferably 8 to 10, carbon atoms, and also further additional esters such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Additionally suitable are esters of $C_{18}$-$C_{38}$-alkylhydroxycarboxylic acids with linear or branched $C_6$-$C_{22}$-fatty alcohols, especially dioctyl malate, esters of linear and/or branched fatty acids with polyhydric alcohols (for example propylene glycol, dimerdiol or trimertriol), triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, especially benzoic acid, esters of $C_2$-$C_{12}$-dicarboxylic acids with polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, for example dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, for example dicaprylyl ether (Cetiol® OE), ring-opening products of epoxidized fatty acid esters with polyols and hydrocarbons or mixtures thereof.

Useful further oil bodies are, for example, silicone oils. They may be present as cyclic and/or linear silicone oils. Silicone oils are high molecular weight synthetic polymeric compounds in which silicon atoms are joined via oxygen atoms in a chain-like and/or grid-like manner and the remaining valences of silicon are satisfied by hydrocarbon radicals (usually methyl, more rarely ethyl, propyl, phenyl groups etc.). Systematically, the silicone oils are referred to as polyorganosiloxanes. The methyl-substituted polyorgano-siloxanes, which are the most important compounds of this group in terms of volume and are characterized by the following structural formula

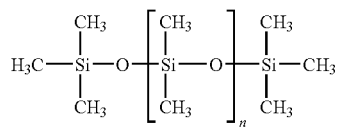

are also referred to as polydimethylsiloxane or dimethicone (INCI). Dimethicones come in various chain lengths and with various molecular weights.

Advantageous polyorganosiloxanes in the context of the present invention are, for example, dimethylpoly-siloxane [poly(dimethylsiloxane)], which are available, for example, under the Abil 10 to 10 000 trade names from Evonik Goldschmidt. Also advantageous are phenylmethylpolysiloxane (INCI: Phenyl Dimethicone, Phenyl Trimethicone), cyclic silicones (octamethyl-cyclotetrasiloxane or decamethylcyclopentasiloxane), which are also referred to in accordance with INCI as Cyclomethicone, amino-modified silicones (INCI: Amodimethicone) and silicone waxes, e.g. polysiloxane-polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are available as various Abil wax grades from Evonik Goldschmidt. However, other silicone oils can also be used advantageously in the context of the present invention, for example cetyldimethicone, hexamethylcyclotrisiloxane, polydimethylsiloxane, poly(methylphenylsiloxane). Silicones which are particularly preferred in accordance with the invention are dimethicone and cyclomethicone.

The inventive formulations may further comprise biogenic active ingredients, insect repellents, tyrosinase inhibitors, preservatives, perfume oils, superfatting agents, stabilizers and/or hydrotropes.

The invention therefore further provides cosmetic and/or pharmaceutical formulations comprising 0.1 to 80% by weight of hydrocarbons which comprise linear C11 and linear C13 hydrocarbons, where the sum of the linear C11 and linear C13 hydrocarbons is greater than or equal to 60% by weight, based on the sum of the hydrocarbons, and at least one biogenic active ingredient, insect repellent, tyrosinase inhibitor, preservative, perfume oil, stabilizer and/or hydrotrope.

Biogenic active ingredients are understood to mean, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example Aloe Vera, prunus extract, bambara nut extract and vitamin complexes.

Useful insect repellents include, for example, N,N-dimethyl-m-toluamide, 1,2-pentanediol or ethyl 3-(N-n-butyl-N-acetylamino)propionate), which is sold under the Insect Repellent® 3535 name by Merck KGaA, and butylacetylaminopropionates.

Useful tyrosine inhibitors which prevent the formation of melanine and find use in depigmenting agents include, for example, arbutin, ferulic acid, kojic acid, cumaric acid and ascorbic acid (vitamin C).

Suitable preservatives are, for example, phenoxyethanol, formaldehyde solution, parabens, pentanediol or sorbic acid, and the silver complexes known under the Surfacine® name. Additionally suitable as preservatives are the 1,2-alkanediols having 5 to 8 carbon atoms, which are described in WO 07/048,757.

Suitable preservatives are especially the substances approved according to Annex VI of the Commission Directive (in the version: Commission Directive 2007/22/EC of 17 Apr. 2007 amending Council Directive 76/768/EEC, concerning cosmetic products, for the purposes of adapting Annexes IV and VI thereto to technical progress), to which reference is made here explicitly.

Perfume oils include mixtures of natural and synthetic odorants. Natural odorants are extracts from flowers, stems and leaves, fruit, fruit shells, roots, wood, herbs and grasses, needles and branches, resins and balsams. Additionally useful are animal raw materials, for example civet and castoreum, and synthetic odorant compounds of the ester, ether, aldehyde, ketone, alcohol and hydrocarbon type.

The stabilizers used may be metal salts of fatty acids, for example stearates or ricinoleates of magnesium, aluminum and/or zinc.

To improve the flow behavior, it is also possible to use hydrotropes, for example ethanol, isopropyl alcohol or polyols. Polyols which are useful here possess preferably 2 to 15 carbon atoms and at least two hydroxyl groups. The polyols may contain further functional groups, especially amino groups, or be modified with nitrogen.

EXAMPLES

Preparation Example 1

Preparation of an Inventive Hydrocarbon Mixture

To prepare an inventive hydrocarbon mixture, tridecane and undecane were first prepared separately from one another from the particular fatty alcohols, and then mixed in the desired ratio relative to one another.

1a) Preparation of Tridecane from 1-tetradecanol 1000 g of 1-tetradecanol (4.7 mol; Lorol C 14 from Cognis) were initially charged in a stirrable pressure vessel with 10 g of a nickel catalyst (Ni-5249 P from Engelhard; Ni content=63% by weight) and heated to 240° C. Subsequently, hydrogen was added via a sparging tube at a pressure of 20 bar over a period of 12 h, and the reaction gases were simultaneously discharged through a valve on the reactor lid. Thereafter, the product was cooled, discharged and filtered. This gave a final weight of 845 g of reaction product.

A GC analysis shows the following composition: 89.0% tridecane, 2.1% tetradecane, 4.1% 1-tetradecanol, 4.2% dimeric reaction products. This reaction product was fractionated in a distillation to give pure tridecane, and then deodorized with nitrogen. This gives a colorless, mobile and low-odor product.

1b) Preparation of Undecane from 1-dodecanol 1000 g of 1-dodecanol (5.4 mol; Lorol C 12 from Cognis) were initially charged in a stirrable pressure vessel with 10 g of a nickel catalyst (Ni-5249 P from Engelhard; Ni content=63% by weight) and heated to 240° C. Subsequently, hydrogen was added via a sparging tube at a pressure of 20 bar over a period of 12 h, and the reaction gases were simultaneously discharged through a valve on the reactor lid. Thereafter, the product was cooled and discharged and filtered. This gave a final weight of 835 g of reaction product.

A GC analysis shows the following composition: 68.4% undecane, 0.6% dodecane, 21.7% 1-dodecanol, 7.2% dimeric reaction products. This reaction product was distilled in order to obtain undecane in pure form. This was then deodorized with nitrogen. This gives a colorless, mobile and low-odor product.

The compounds obtained according to example 1a) and according to example 1b) were used to prepare the following inventive hydrocarbon mixture:

Composition of the hydrocarbon mixture according to example 1: 76% by weight of n-undecane, 24% by weight of n-tridecane.

Preparation Example 2

To prepare an inventive hydrocarbon mixture, a fatty alcohol mixture which comprises C12 and C14 fatty alcohols correspondingly to the hydrocarbon mixture to be prepared was subjected to a reductive dehydroxymethylation.

1000 g of Lorol® Spezial (from Cognis; fatty alcohol distribution C 12 70-75%, C 14 24-30%, C16 less than 4%) and 10 g of a nickel catalyst (Ni-5249 P from Engelhard; Ni content=63% by weight) were initially charged in an autoclave. The reactor was closed and evacuated. The reaction mixture was then heated to approx. 80° C. under reduced pressure and stirred for 30 min. Thereafter, the reactor was brought to approx. 80 bar with hydrogen and heated continuously to 250° C. The reaction is complete when the pressure remains constant and the majority of the fatty alcohol has been converted to the desired hydrocarbon. After decompressing and venting with nitrogen, the product was purified by distillation. The purified product is obtained as a colorless liquid.

The hydrocarbon mixture obtainable according to preparation example 2 has the following composition (GC analysis):

| Hydrocarbons with a carbon number of | Proportion in the sum total of the hydrocarbons [% by weight] |
|---|---|
| C11 (linear) | 67 |
| C12 | 4 |
| C13 (linear) | 26 |
| C14 | 1.5 |
| C9, C10, C15 | 1.5 |

The weight ratio of linear C11 hydrocarbon to linear C13 hydrocarbon is 2.57. The weight ratio of the C12 hydrocarbons to the C14 hydrocarbons is likewise 2.57.

Use Example 1

The mixture of n-undecane and n-tridecane obtained according to preparation example 2 was used for the following deodorant stick formulation, and the hardness of the formulations thus obtained was tested (all figures in percent by weight):

| Ingredients INCI [trade name] | Inventive example | Comparative example |
|---|---|---|
| Stearyl alcohol [Lanette ® 18] | 14.7 | 14.7 |
| Hydrogenated castor oil [Cutina ® HR] | 3.7 | 3.7 |
| Cyclomethicone [Dow Corning ® 245] | — | 58.7 |
| n-Undecane/n-tridecane according to preparation example 2 | 58.7 | — |
| Aluminum zirconium tetrachlorohydrex GLY [Rezal ® 36 GP] | 22.9 | 22.9 |
| Hardness | 4.0 | 3.5 |

The hardness (indentation depth) was determined according to the Deutsche Einheitsmethoden zur Untersuchung von Fetten, Fettprodukten, Tensiden and verwandten Stoffen [German standard methods for analyzing fats, fat products, surfactants and related substances], Bestimmung der Härte von Wachsen [Determination of the hardness of waxes], Nadel-Penetration [Needle penetration] M-III 9b (98).

Use Example 2

The cream produced according to the formulation below was tested by a panel of 5 sensorily skilled subjects and assessed as sensorily "light".

All-purpose Cream (W/O)

| Phase | Component/ trade name | INCI | % by wt. |
|---|---|---|---|
| I. | DEHYMULS ® E | Dicocoyl pentaerythrityl distearyl citrate (and) sorbitan sesquioleate (and) cera alba (beeswax) (and) aluminum stearate | 3.00 |

-continued

| Phase | Component/ trade name | INCI | % by wt. |
|---|---|---|---|
| | DEHYMULS ® PGPH | Polyglyceryl 2 dipoly-hydroxystearate | 2.00 |
| | CETIOL ® OE | Dicaprylyl ether | 5.00 |
| | CETIOL ® 868 | Ethylhexyl stearate | 5.00 |
| | MYRITOL ® 331 | Cocoglycerides | 1.00 |
| | Hydrocarbon mixture according to preparation example 1 or preparation example 2 | | 6.00 |
| II. | Glycerol 86% | | 5.00 |
| | MgSO$_4$ × 7H$_2$O | | 1.00 |
| | Water, deionized | | 72.00 |
| III. | Preservative | | q.s. |

Production: The components of phase I were melted at 80 to 85° C. and stirred for homogeneity. The components of phase II were heated to 80 to 85° C. and added slowly with stirring to phase I. The mixture was stirred at this temperature for a further 5 minutes. Thereafter, the emulsion was cooled with stirring and homogenized at 65 to 55° C. As soon as the emulsion appeared homogeneous, it was cooled further to 30° C. with stirring. Thereafter, components of phase III were added and the mixture was stirred again.

Formulation Examples

Balsam for moistening and for protection of the lips

| Phase | Component | INCI | % by wt. |
|---|---|---|---|
| I. | Cerilla Raffinée G* | Candelilla (*Euphorbia Cerifera*) wax | 7.53 |
| | CUTINA ® LM conc. | Polyglyceryl-2 dipolyhydroxystearate and octyldodecanol and *Copernicia Cerifera* (Carnauba) wax and *Euphorbia Cerifera* (Candelilla) wax and beeswax and cetearyl glucoside and cetearyl alcohol | 6.57 |
| | Colophane claire type Y | Rosin | 1.89 |
| | Cerauba T1* | Carnauba (*Copernica Cerifera*) wax | 1.86 |
| | Cerabeil blanche 1* | Beeswax | 5.31 |
| | Hydrocarbon mixture according to preparation example 1 or 2 | | 15.57 |
| | EUTANOL ® G | Octyldodecanol | 21.71 |
| | Crodamol ML (Croda) | Myristyl lactate | 1.13 |
| | ELESTAB ® 366 | | 0.43 |
| II. | Castor oil | Castor oil | 35.00 |
| III. | IRWINOL ® LS 9319 | African wild mango butter | 3.00 |

*obtainable from Lambert-Rivière (France)

Production: Phase I was melted at 85° C., phase II was added and the temperature was kept at 80° C. Phase III was added shortly before introduction into the mold (which was moistened with 50 cts dimethicone and preheated to 40° C.) The material was introduced into the mold and cooled to 40° C. The molds were cooled to close to 0° C. in a freezer.

Styling Wax

| Phase | Component | INCI | % by wt. |
|---|---|---|---|
| I. | CUTINA ® MD | Glyceryl stearate | 47.0 |
| | COMPERLAN ® 100 | Cocamide MEA | 2.50 |
| | CUTINA ® HR powder | Hydrogenated castor oil | 2.50 |
| | PLANTACARE ® 1200 UP | Lauryl glucoside | 5.00 |
| | LANETTE ® O | Cetearyl alcohol | 7.00 |
| | CUTINA ® CP | Cetyl palmitate | 7.00 |
| | EUMULGIN ® O 20 | Oleth-20 | 5.00 |
| | Hydrocarbon mixture according to preparation example 1 or 2 | | 23.5 |
| | Wacker Siliconoil AK 350 | Dimethicone | 0.50 |

The production was effected by heating all the components to 80° C. and homogenizing.

Moisturizing Body Milk

| Phase | Component | INCI | % by wt. |
|---|---|---|---|
| | EMULGADE ® CM | Cetearyl isononanoate (and) ceteareth-20 (and) cetearyl alcohol (and) glyceryl stearate (and) glycerol (and) ceteareth | 5.0 |
| | EUMULGIN ® VL 75 | Lauryl glucoside (and) polyglyceryl-2-dipolyhydroxystearate (and) glycerol | 2.0 |
| | CETIOL ® OE | Dicaprylyl ether | 4.0 |
| | CETIOL ® J 600 | Oleyl erucate | 1.0 |
| | ISOPROPYLMYRISTATE | Isopropyl myristate | 7.0 |
| | Hydrocarbon mixture according to preparation example 1 or 2 | | 7.0 |
| II. | Water, deionized | | ad 100 |
| III. | Cosmedia SP | Sodium polyacrylate | 0.4 |
| IV. | HISPAGEL ® 200 | Glycerol (and) glyceryl polyacrylate | 20.0 |
| V. | Preservative, perfume pH 5.5 | | q.s. |

The production was effected by mixing phase I and water at room temperature with stirring. Then phase III was added and the mixture was stirred until said mixture was homogeneous and swollen. Then phase IV was added, followed by phase V, then the pH was adjusted.

O/W Soft Cream

| Phase | Component | INCI | % by wt. |
|---|---|---|---|
| I. | EMULGADE ® SE-PF | Glyceryl stearate (and) ceteareth-20 (and) ceteareth-12 (and) stearyl alcohol (and) ceteareth-20 (and) distearyl ether | 6.0 |
| | LANETTE ® O | Cetearyl alcohol | 1.0 |

-continued

| Phase | Component | INCI | % by wt. |
|---|---|---|---|
| | CUTINA ® MD | Glyceryl stearate | 2.0 |
| | CETIOL ® MM | Myristyl myristate | 2.0 |
| | | Hydrocarbon mixture according to preparation example 1 or 2 | 8.0 |
| | Jojoba oil | *Simmondsia Chinensis* (jojoba) seed oil | 2.0 |
| | COPHEROL ® 1250 | Tocopheryl acetate | 0.5 |
| | | Dimethicone | 0.5 |
| | | Cyclomethicone | 3.0 |
| II. | Water | Aqua | ad 100 |
| | | Propylene glycol | 3.0 |
| III. | HISPAGEL ® 200 | Glycerol (and) glyceryl polyacrylate | 15.0 |
| IV. | Preservative | | q.s. |
| | | pH 5.5-6.5 | |

This cream was produced by heating phase I to 80° C., likewise heating phase II to 80° C., and adding it to phase I with stirring. This mixture was cooled with stirring and homogenized at approx. 55° C. with a suitable dispersing unit (e.g. Ultra Turrax). Then phase III was added with continuous stirring, phase IV was added and the pH was adjusted.

W/O Cream

| Phase | Component/ trade name | INCI | % by wt. |
|---|---|---|---|
| I. | MONOMULS ® 90 O 18 | Glyceryl oleate | 2.00 |
| | LAMEFORM ® TGI | Polyglyceryl 3 diisostearate | 4.00 |
| | CETIOL ® A | Hexyl laurate | 12.00 |
| | | Hydrocarbon mixture according to preparation example 1 or 2 | 12.00 |
| | SIPOL ® C 16/18 OR | Cetearyl alcohol | 1.00 |
| | Zinc stearate | Zinc stearate | 2.00 |
| | Zinc oxide | CI 77947 (or) zinc oxide | 15.00 |
| | Magnesium sulfate | Magnesium sulfate | 1.00 |
| | Glycerol | Glycerin | 3.00 |
| | Preservative | | q.s. |
| | Benzyl alcohol | Benzyl alcohol | 0.40 |
| | HYDAGEN ® B | Bisabolol | 0.50 |
| | Water | Aqua | 100.00 |

The first 7 components were melted at 85° C. Magnesium sulfate and glycerol were dissolved in water, and this mixture was heated to 85° C. This aqueous phase was added to the oil phase and dispersed. With continuous stirring, the mixture was cooled to 40° C., and then benzyl alcohol and Hydagen B were mixed and added to the emulsion. With further stirring, the mixture was cooled down to 30° C. and homogenized.

"Body Wash" Cleaning Emulsion

| Phase | Component | INCI | % by wt. |
|---|---|---|---|
| I. | Texapon ALS-IS | Ammonium lauryl sulfate | 30.00 |
| | TEXAPON ® NSO | Sodium laureth sulfate | 18.00 |
| | | Hydrocarbon mixture according to preparation example 1 or 2 | 18.00 |
| | Plantacare ® 1200 | Lauryl glucoside | 8.00 |
| II. | Jaguar HP 105 | Hydroxypropyl guar | 2.00 |
| | Euxyl K400 | Methyldibromoglutaronitrile and phenoxyethanol | 0.10 |
| | Water | Aqua | 23.90 |
| | pH value | 5.6 | |

What is claimed is:

1. A hydrocarbon mixture comprising linear C11 and linear C13 hydrocarbons, the sum of the linear C11 and linear C13 hydrocarbons being greater than or equal to 75% by weight, based on the sum of the hydrocarbons, and wherein the hydrocarbon mixture comprises, based on the sum of the hydrocarbons:
   a. 55 to 80% by weight of linear C11 hydrocarbons; and
   b. 20 to 45% by weight of linear C13 hydrocarbons.

2. The hydrocarbon mixture of claim 1, wherein the sum of the branched hydrocarbons, wherein the sum of the branched hydrocarbons present in the hydrocarbon mixture is is less than or equal to 20% by weight, based on the sum of the hydrocarbons.

3. The hydrocarbon mixture of claim 1, wherein the sum of the aromatic hydrocarbons, wherein the sum of aromatic hydrocarbons present in the hydrocarbon mixture is less than or equal to 20% by weight, based on the sum of the hydrocarbons.

4. The hydrocarbon mixture of claim 1, further comprising unsaturated hydrocarbons, wherein the sum of aromatic hydrocarbons present in the hydrocarbon mixture is less than or equal to 20% by weight, based on the sum of the hydrocarbons.

5. The hydrocarbon mixture of claim 1, further comprising even-numbered hydrocarbons, wherein the sum of the even-numbered hydrocarbons present in the hydrocarbons is less than or equal to 20% by weight, based on the sum of the hydrocarbons.

6. The hydrocarbon mixture of claim 1, wherein said linear C11 and/or linear C13 hydrocarbons are saturated hydrocarbons.

7. The hydrocarbon mixture of claim 1, further comprising C12 hydrocarbons, wherein the proportion of C12 hydrocarbons present in the hydrocarbon mixture is less than or equal to 10% by weight, based on the sum of the hydrocarbons.

8. The hydrocarbon mixture of claim 1, further comprising hydrocarbons having a carbon chain length greater than or equal to 14 , wherein the sum of hydrocarbons having a carbon chain length greater than or equal to 14 present in the hydrocarbon mixture less than or equal to 15% by weight, based on the sum of the hydrocarbons.

9. The hydrocarbon mixture of claim 1, further comprising hydrocarbons having a carbon chain length greater than or equal to 10 wherein the sum of hydrocarbons having a carbon chain length greater than or equal to 10 present in the hydrocarbon mixture is less than or equal to 3% by weight, based on the sum of the hydrocarbons.

10. A method of preparing a cosmetic and/or pharmaceutical formulation comprising adding the hydrocarbon mixture of claim 1 to a cosmetic and/or pharmaceutical base.

11. A cosmetic and/or pharmaceutical formulation comprising 0.1 to 80% by weight of a hydrocarbons which comprising linear C11 and linear C13 hydrocarbons, where the sum of the linear C11 and linear C13 hydrocarbons is greater than or equal to 75% by weight, based on the sum of the hydrocarbons, and wherein the hydrocarbon mixture comprises, based on the sum of hydrocarbons:
- a. 55 to 80% by weight of linear C11 hydrocarbons; and
- b. 20 to 45% by weight of linear C13 hydrocarbons.

12. The cosmetic and/or pharmaceutical formulation of claim 11 comprising at least one antiperspirant or deodorant active ingredient.

13. The cosmetic and/or pharmaceutical formulation of claim 11 comprising at least one UV light protection filter.

14. The cosmetic and/or pharmaceutical formulation of claim 11 comprising at least one emulsifier and/or surfactant and/or wax component and/or polymer and/or further oil body.

15. The hydrocarbon mixture of claim 1, further comprising branched hydrocarbons, wherein the sum of branched hydrocarbons present in the hydrocarbon mixture is less than or equal to 1% by weight, based on the sum of the hydrocarbons.

16. The hydrocarbon mixture of claim 1, wherein the sum of the aromatic hydrocarbons, wherein the sum of aromatic hydrocarbons present in the hydrocarbon mixture is less than or equal to 1% by weight, based on the sum of the hydrocarbons.

17. The hydrocarbon mixture of claim 1, wherein the sum of the unsaturated hydrocarbons, wherein the sum of unsaturated hydrocarbons present in the hydrocarbon mixture is less than or equal to 1% by weight, based on the sum of the hydrocarbons.

18. The hydrocarbon mixture of claim 1, further comprising even-numbered hydrocarbons, wherein the sum of even-numbered hydrocarbons present in the hydrocarbon mixture is less than or equal to 5% by weight, based on the sum of the hydrocarbons.

19. The hydrocarbon mixture of claim 1, further comprising C12 hydrocarbons, wherein the proportion of C12 hydrocarbons present in the hydrocarbon mixture is less than or equal to 3% by weight, based on the sum of the hydrocarbons.

20. The method of claim 10 wherein said hydrocarbon mixture is added as an oil body and/or dispersant.

* * * * *

UNITED STATES PATENT AND TRADEMARK OFFICE
CERTIFICATE OF CORRECTION

PATENT NO. : 8,309,065 B2
APPLICATION NO. : 12/665425
DATED : November 13, 2012
INVENTOR(S) : Achim Ansmann et al.

Page 1 of 1

It is certified that error appears in the above-identified patent and that said Letters Patent is hereby corrected as shown below:

In the Claims:

Column 34: In Claim 2, line 23, delete "is" 2nd occurrence

Column 34: In Claim 4, line 32, replace "aromatic" with --unsaturated--

Column 34: In Claim 5, line 38, replace the second "hydrocarbons" with --hydrocarbon mixture--

Column 34: In Claim 11, line 64, replace "hydrocarbons which" with --hydrocarbon mixture--

Column 35: In Claim 16, lines 21-22, replace "wherein the sum of the" with --further comprising--

Column 36: In Claim 17, lines 4-5, replace "wherein the sum of the" with --further comprising--

Signed and Sealed this
Twenty-first Day of May, 2013

Teresa Stanek Rea
*Acting Director of the United States Patent and Trademark Office*